United States Patent
Srivastava et al.

(10) Patent No.: US 9,018,226 B2
(45) Date of Patent: Apr. 28, 2015

(54) **ANTIPSYCHOTIC AGENTS AND STANDARDIZED ANTIPSYCHOTIC FRACTIONS FROM *RAUWOLFIA TETRAPHYLLA* AND PROCESS OF THEIR ISOLATION**

(75) Inventors: Santosh Kumar Srivastava, Lucknow (IN); Ashok Kumar Agrawal, Lucknow (IN); Subhash Chandra Singh, Lucknow (IN); Vinay Kumar Khanna, Lucknow (IN); Janardan Singh, Lucknow (IN); Chandeshwar Nath, Lucknow (IN); Madan Mohan Gupta, Lucknow (IN); Shikha Gupta, Lucknow (IN); Ram Kishor Verma, Lucknow (IN); Anirban Pal, Lucknow (IN); Dnyaneshwar Umrao Bawankule, Lucknow (IN); Dharmendra Saikia, Lucknow (IN); Anil Kumar Gupta, Lucknow (IN); Anupam Maurya, Lucknow (IN); Suman Preet Singh Khanuja, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 583 days.

(21) Appl. No.: 13/262,040

(22) PCT Filed: Mar. 31, 2010

(86) PCT No.: PCT/IN2010/000208
§ 371 (c)(1),
(2), (4) Date: Mar. 1, 2012

(87) PCT Pub. No.: WO2010/113180
PCT Pub. Date: Oct. 7, 2010

(65) Prior Publication Data
US 2012/0184576 A1 Jul. 19, 2012

(30) Foreign Application Priority Data

Mar. 31, 2009 (IN) .............................. 658/DEL/2009

(51) Int. Cl.
A61K 31/4375 (2006.01)
C07D 491/22 (2006.01)
A61K 36/24 (2006.01)

(52) U.S. Cl.
CPC ...................................... A61K 36/24 (2013.01)

(58) Field of Classification Search
USPC ........................................... 514/280; 546/48
See application file for complete search history.

(56) References Cited

PUBLICATIONS

Akinloye, B.A. et al.: Stem bark alkaloids of *Rauwolfia volkensii*. Planta Medica, vol. 37, pp. 361-366, 1979.*

* cited by examiner

Primary Examiner — Charanjit Aulakh
(74) Attorney, Agent, or Firm — Abelman, Frayne & Schwab

(57) ABSTRACT

The present invention relates to bioactive extracts its fractions and isolation of compound from *Rauwolfia tetraphylla*. The extracts and fractions are useful for the treatment of psychosis based on in-vivo validation on animal model and proportional binding affinities for dopaminergic-$D_2$, Cholinergic (muscarinic) and Serotonergic ($5HT_{2A}$) receptors for antipsychotic activity. The present invention relates to novel antipsychotic activity in the leaf alkaloids of Formula 1 and 2 named tetrahydroalstonine, 10-methoxytetrahydroalstonine, isoreserpiline, 10-demethoxyreserpiline, 11-demethoxyreserpiline, reserpiline and α-yohimbine. The present invention also relates to processes for obtaining antipsychotic extracts as well as for the isolation of alkaloids of formula 1 and 2 from the leaves of *Rauwolfia tetraphylla*. The present invention particularly relates to significant antipsychotic activity in the MeOH extract, ethylacetate and chloroform fractions of *R. tetraphylla* and in the isolated compounds α-yohimbine, reserpiline and in a mixture 10-demethoxyreserpiline and 11-demethoxyreserpiline in 1:1.5 ratios for treating psychosis without any extra pyramidal symptoms (EPS).

Formula-1

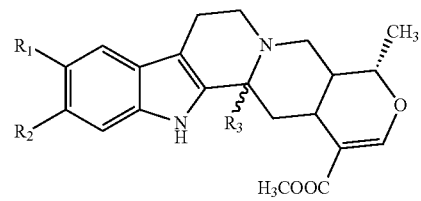

1. $R_1 = R_2 = OMe$ $R_3 = \alpha$-H (Isoreserpiline)
2. $R_1 = R_2 = OMe$ $R_3 = \beta$-H (Reserpiline)
3. $R_1 = OMe$ $R_2 = H$ $R_3 = \beta$-H (11-Demethoxy reserpiline)
4. $R_1 = H$ $R_2 = OMe$ $R_3 = \beta$-H (10-Demethoxy reserpiline)
5. $R_1 = R_2 = H$ $R_3 = \alpha$-H (Tetrahydroalstonine)
7. $R_1 = OMe$ $R_2 = H$ $R_3 = \alpha$-H (10-Methoxytetrahudroalstonine)

Formula 2

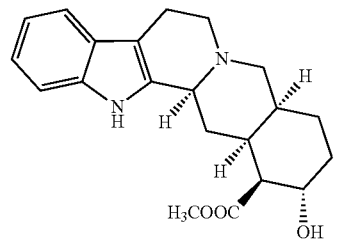

(6. α-Yohimbine)

21 Claims, 8 Drawing Sheets

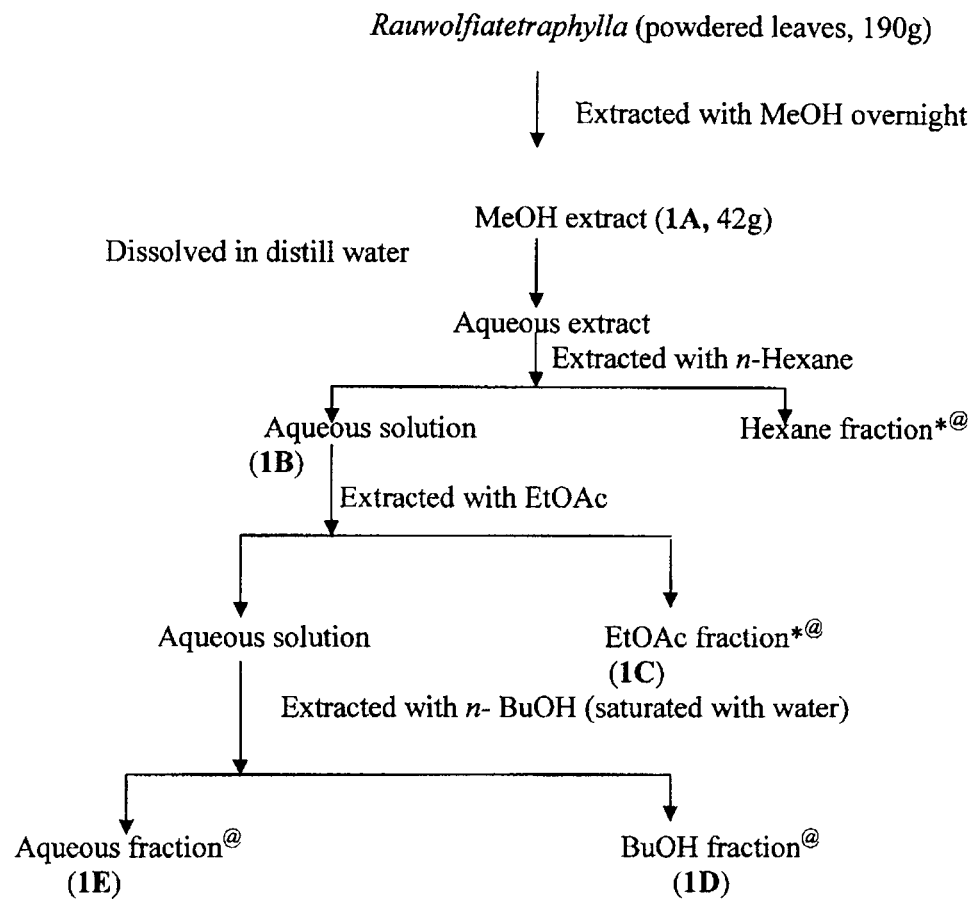
Fig 8: Flow chart 1

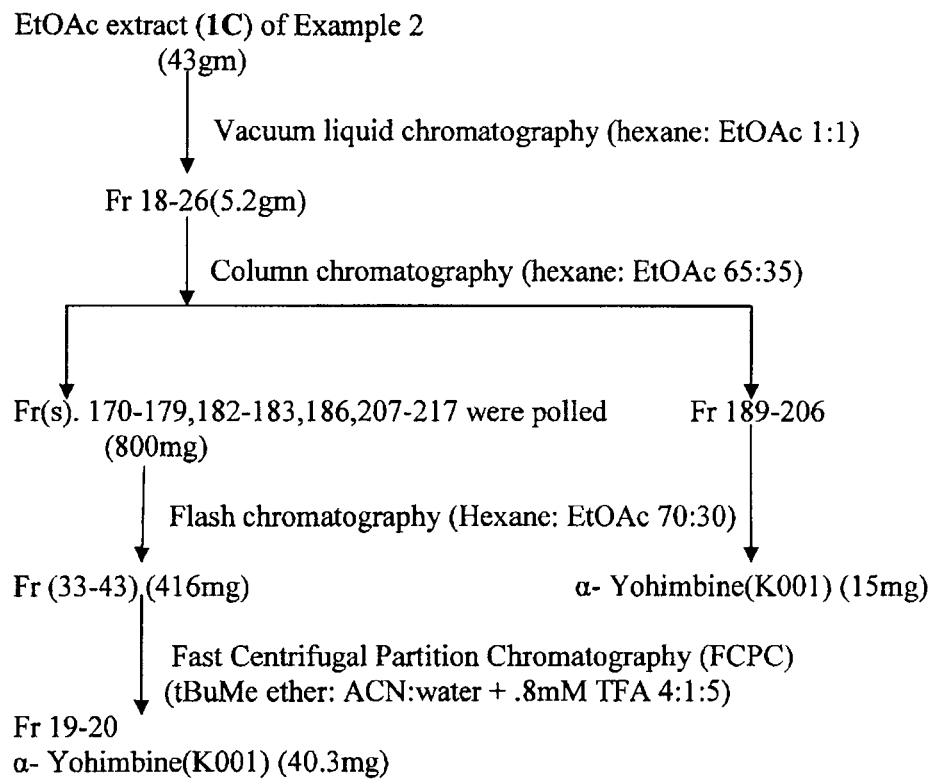
Fig :9 Flow chart 2

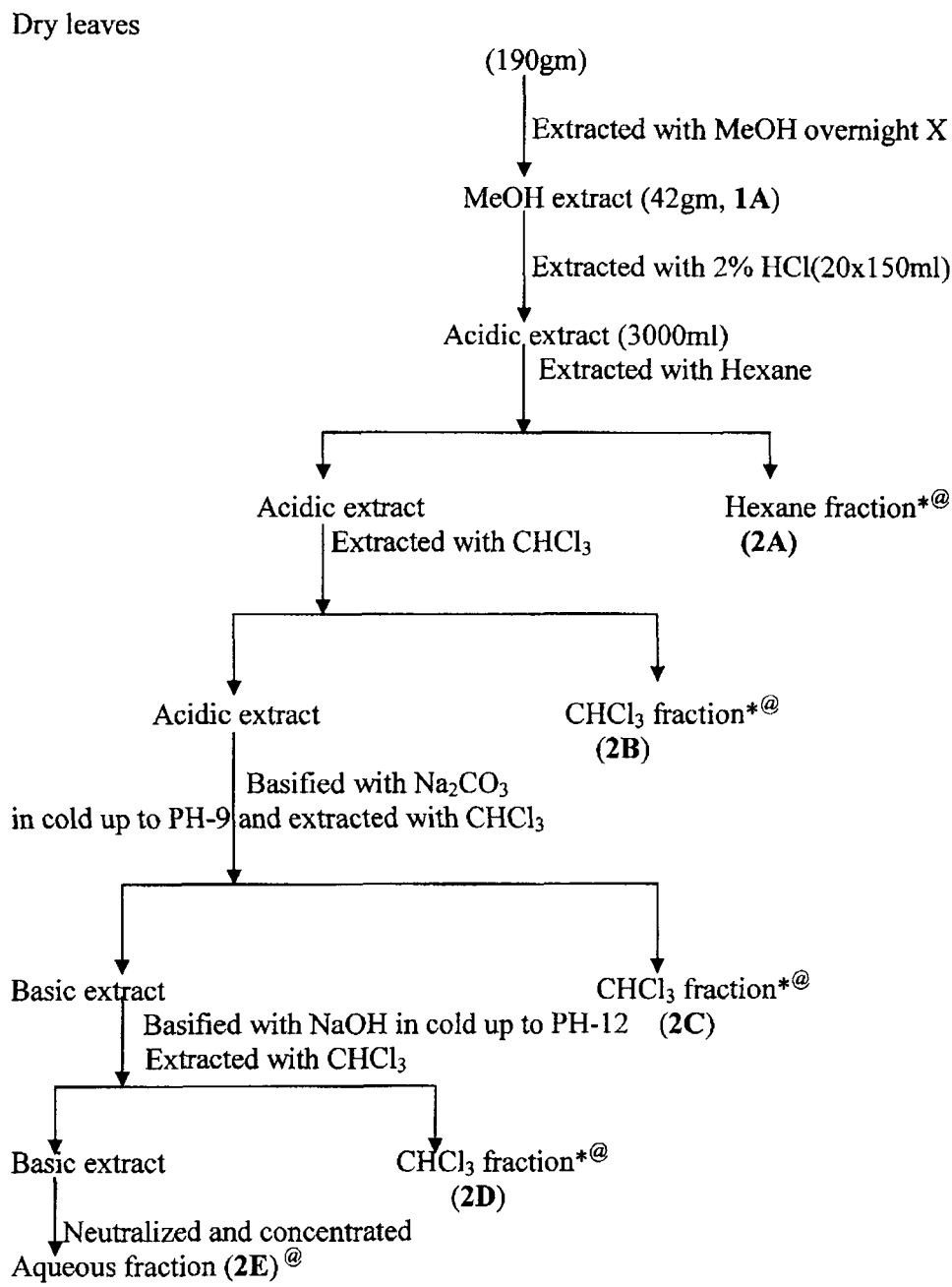
Fig 10: Flow chart 3

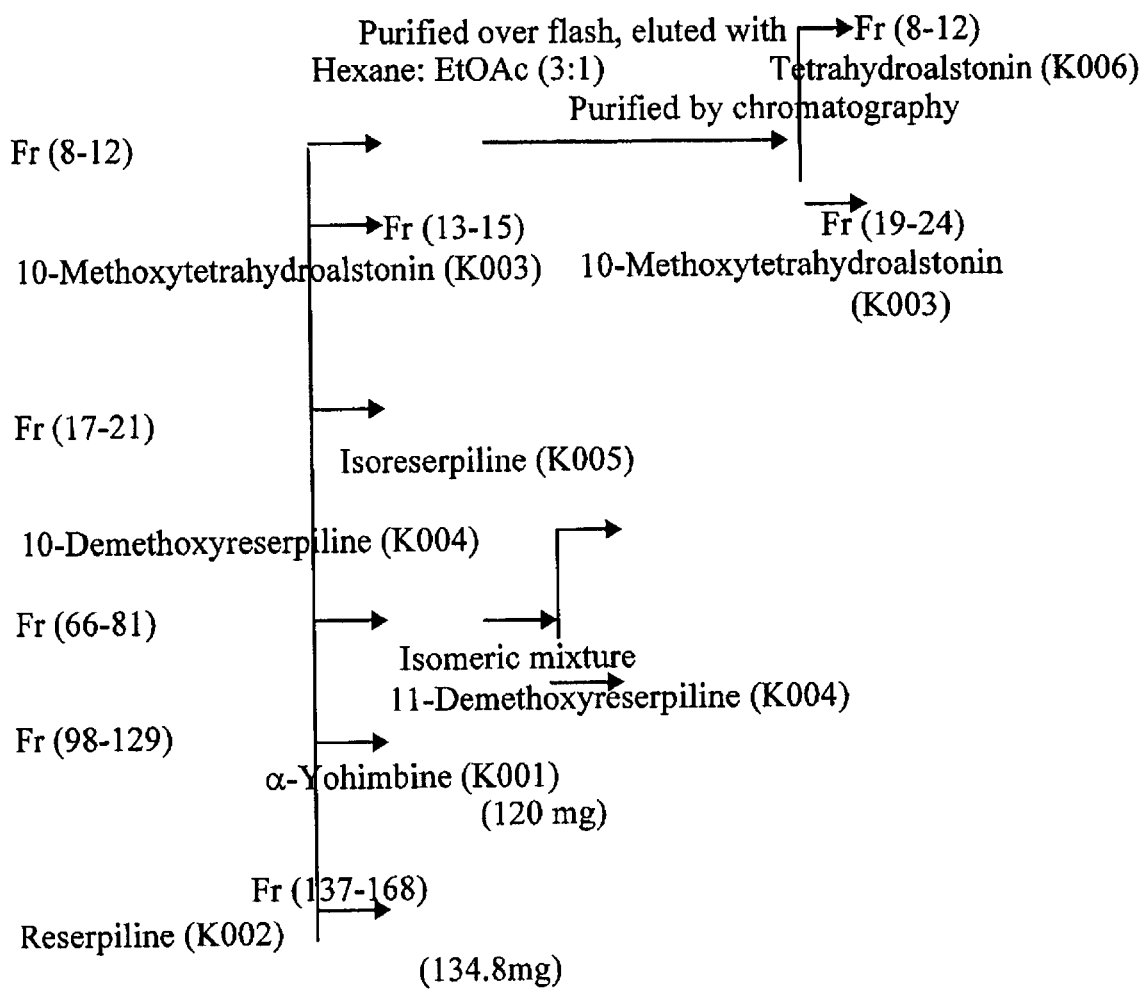
Fig. 11: Flow chart 4

ANTIPSYCHOTIC AGENTS AND STANDARDIZED ANTIPSYCHOTIC FRACTIONS FROM *RAUWOLFIA TETRAPHYLLA* AND PROCESS OF THEIR ISOLATION

RELATED APPLICATIONS

This application is a §371 of PCT/IN2010/000208 filed Mar. 31, 2010, and claims priority from Indian Patent Application No. 658/DEL/2009 filed Mar. 31, 2009, both incorporated by reference in their entirety.

FIELD OF INVENTION

The present invention relates to novel antipsychotic activity in the leaf extracts of *Rauwolfia tetraphylla* and their useful standardized herbal formulations for the treatment of psychosis based on proportional binding affinities for dopaminergic-$D_2$ and Serotonergic ($5HT_{2A}$) receptors in vitro and amphitamine induced hyperactive mouse model in-vivo for antipsychotic activity. The present invention further relates to a process for obtaining antipsychotic extracts from the leaves of *R. tetraphylla*, which are non toxic and devoid of extra pyramidal side effects. The present invention also relates to novel antipsychotic activity in the leaf alkaloids of Formula 1 and 2 named tetrahydroalstonine, 10-methoxytetrahydroalstonine, isoreserpiline, 10-demethoxyreserpiline, 11-demethoxyreserpiline, reserpiline and α-yohimbine. The present invention further relates to processes for obtaining antipsychotic extracts as well as for the isolation of alkaloids of formula 1 and 2 from the leaves of *R. tetraphylla*. The present invention particularly relates to significant antipsychotic activity in the MeOH extract, ethylacetate and chloroform fractions of *R. tetraphylla* and in the isolated compounds α-yohimbine, reserpiline and in a mixture 10-demethoxyreserpiline and 11-demethoxyreserpiline in 1:1.5 ratios for treating psychosis without any extra pyramidal symptoms (EPS).

BACKGROUND OF INVENTION

Psychosis is one of the most dreaded disease of the 20th century and spreading further with continuance and increasing incidences in 21st century. Psychosis means abnormal condition of the mind. People suffering from psychosis are said to be psychotic. A wide variety of central nervous system diseases, from both external toxins, and from internal physiologic illness, can produce symptoms of psychosis. It is considered as an adversary of modernization and advanced pattern of socio-cultured life dominated by western medicine. Multidisciplinary scientific investigations are making best efforts to combat this disease, but the sure-shot perfect cure is yet to be brought in to world of medicine.

Natural antipsychotic agents are an important area of the current research and are in good demand all over the world because they are better than synthetic drugs as they do not possess serious side effects and chronic toxicity. To the best of our knowledge there are many antipsychotic drugs but all are synthetic, so there is need to search for the potential antipsychotic drug from the plants.

Indole alkaloids are aromatic hetrocyclic organic compounds and occur in a large number of plant families. Many reviews have dealt with their distribution, structure, properties and biosynthesis. The indole structure can be found in many organic compounds like amino acid tryptophan and in tryptophan containing protein, in alkaloids and in pigments. They have been reported to possess various biological activities such as antitumor, antimicrobial, antihypertensive (Verpoorte, R. In Alkaloids: Biochemistry, Ecology and Medicinal Applications; Roberts, M. F. & Wink, M., (Eds.); Plenum Press; New York, 1998, pp 397-433), antileishmanial activity, antibacterial activity.

The genus *Rauwolfia* belongs to the family Apocynaceae and five species of this genus are native to India. *R. tetraphylla* L. syn. *R. canescens* L. (Compend. Indian Med. Plants, Vol. 1, Rastogi&Mehrotra, PID, New Delhi, 1990, p. 340) is an economically important plant, which is cultivated on commercial scale in India. The plant is important because of the presence of nearly 30 alkaloids in its roots: ajmalicine, reserpine, sapagine, deserpidine, rescinnamine, serpentine, ajmalidine, alloyohimbine, chandrine, corynathine, iscajmaline, neo ajmaline, papaverine, raunatine, raunoline, rauwolscine or (α-yohimbine), reserpiline, reserpinine, reserpoxidine, serpinine, serpentinine, thambine, ajmaline and yohimbine [(Farooqi and Sreeramu, 2001, Cultivation of Medicinal and Aromatic Crops. University Press Ltd., India, pp: 210-211), J. Amer. Chem. Soc. 79(5):1217-1222].

From the leaves of *R. tetraphylla* N(α)-demethylaccidine, tetraphylline, tetraphyllicine [(Phytochemistry, 28(3): 1989, 961-962), J. Amer. Chem. Soc. 79(5): 1217-1222], aricine, isoreserpiline, tetrahydroalstonine, a yohimbine isomer (Rev. Cubana Farm. 1982, 16, 28; Chem. Abstr. 1982, 97, 107095 q; Rev. Cubana Farm. 1982, 16, 316; Chem. Abstr. 1983, 98, 176193 c); α-yohimbine and reserpiline have been isolated (Rev. Cubana Farm. 1982, 16, 251; Chem. Abstr. 1983, 98, 157873 h), (Compendium of Indian Medicinal Plants: Vol. 3 1980-1984 by Ram P. Rastogi, B. N. Mehrotra).

Yohimbine has been used to facilitate recall of traumatic memories in the treatment of posttraumatic stress disorder (PTSD). Yohimbine is used in arteriosclerosis and angina pectoris, and has been used as a local anesthetic and mydriatic and for its purported aphrodisiac properties (http://www.lookchem.com/YOHIMBINE/). According to one study, oral yohimbine supplementation may actuate significant fat loss in athletes (Ostojic S M, Res Sports Med. 2006, 14 (4): 289-99). In veterinary medicine, yohimbine is used to reverse anesthesia from the drug xylazine in small and large animals. Yohimbine hydrochloride is a selective competitive alpha-2 adrenergic receptor antagonist. The alpha-2 receptor is responsible for sensing adrenaline and noradrenaline and telling the body to decrease its production. Yohimbine also antagonizes several serotonin receptor subtypes: 1 A (inhibitory, behavioral control), 1B (inhibitory, vasoconstriction), 1D (inhibitory, vasoconstriction), and 2B (smooth muscle contraction). Since yohimbine is an antagonist, it will decrease the effects of these receptors, thus causing excitation, vasodilation, and smooth muscle relaxation. In addition to all these pharmacological activities, yohimbine creates numerous side effects such as rapid heart rate, high blood pressure, over stimulation, insomnia. Some effects in rare cases were panic attacks, headaches, dizziness and skin flushing. More serious adverse effects may include seizures and renal failure. Yohimbine should not be consumed by anyone with liver, kidney, heart disease or a psychological disorder.

On the other hand, α-yohimbine(17α-hydroxy-20α-yohimban-16β-carboxylic acid methyl ester) or rauwolscine is one of the isomer of yohimbine (17α-hydroxy-20β-yohimban-16α-carboxylic acid methyl ester) and does not possess side effects. It is one of the constituent of *R. tetraphylla* leaves and has shown quite different pharmacological activities to those of yohimbine such as standard $\square_2$-adrenergic antagonist, partial agonist at $5\text{-}HT_{1A}$ receptors. (Arthur et al, 1993, Biochem. Pharmacol. 45: 2337, Hieble et al 1995, J. Med.

Chem. 38, 3415, Uhlen et al, 1998, Eur. J. Pharmacol. 343: 93). α-yohimbine was more potent than RX 781094 in blocking these alpha-2 adrenoceptorsin-vivo where as both compounds were equipotent at alpha-1 adrenoceptors. α-Yohimbine was found about 25 times more selective than RX 781094 and 2 times more alpha-2 adrenoceptors selective than RS 21361. RX 781094 was approximately 3 times more effective than α-yohimbine in antagonizing the centrally mediated alpha-2 adrenoceptor-induced hypotension and sedation of clonidine in rats and mice (Timmermans et al, J Pharmacol Exp Ther., 228, (3), 1984, 739-48). Alpha 2-adrenergic receptor antagonist α-yohimbine may function as an agonist at the serotonin 1A (5-HT$_{1A}$) receptor expressed in human brain. α-Yohimbine and yohimbine are partial agonists for the human 5-HT$_{1A}$ receptor (Biochempharmacol 1993, 45, (11) 2337-41). α-Yohimbine, an alkaloid of R. canescens Linn. (Chatterjee et al Ind. Chem. Soc., 18, (33), 485, 1941) was found to be a potent adrenolytic compound (Chakravarti, Science and Culture, 8, (8), 1942). Rauwolscine behaves as competitive antagonist and displays greater efficacy in relaxing basal tension. (Biochemical pharmacology 66, 2003, 927-937).

Reserpiline is markedly sympatholytic and hypotensive with no noticeable depressant effects on the central nervous system and sedative properties. In comparison with reserpine and rescinnamine it does not induce appearance of gastric ulcers, has no laxative effect and lacks other side effects (African ethnobotany: poisons and drugs: chemistry, pharmacology, toxicology By Hans Dieter Neuwingerpg 133, 1996, chapman & Hall GmbH, Weinheim, Germany). Isoreserpiline and reserpiline have antidiabetic activity (Traditional medicine for modern times, antidiabetic plants. Eds. Amala-Soumyanathpg-56, 2006, CRC Press, Taylor & Francis, Boca Raton Fla., USA).

Alastonine an alkaloid from the genus *Alastonia* possesses antimalarial activity, but is more toxic than quinine as shown in ducklings, mice and rats. (Wakim and Chon, J. Pharmacol. Exptl. Therapeutics 90 (1), 57-67, 1947). The indole alkaloid alastonine has been identified as the major component of a plant-based remedy, used in Nigeria to treat mental illness by traditional psychiatrists. It possesses clear anxiolytic activity, mediated by 5-HT$_{2A/2C}$ serotonin receptors (Elisabetsky and costa-campose CAM 2006; 3(1) 39-48 doi: 10.1093/ecam/nek011). Alastonine is the major component of plants used by Nigerian psychiatrists as anti-dementia drugs. Recent researches have shown that alastonine increases seratonergic transmission and intraneuronal dopamine catabolism. (Linck et al, eCAM 2009; page 1-7 doi:10.1093/ecam/nep002). Experimental data have shown that unlike clozapine, alastonine does not possess pro-convulsant activity and deserves to be scrutinized as a model for the development of newer antipsychotics. (costa-campos et al J. Ethnopharmacol 93: 307-310, 2004).

To the best of our knowledge there is no report for the antipsychotic activity in the leaf extract of R. tetraphylla and in the compounds isolated from the leaf extracts of R. tetraphylla: α-yohimbine, reserpiline and a mixture of 10-demethoxyreserpiline and 11-demethoxyreserpiline in 1:1.5 ratios. Hence we wish to report the antipsychotic activities in the leaf extracts of R. tetraphylla and in α-yohimbine, reserpiline and a mixture of 10-demethoxyreserpiline and 11-demethoxyreserpiline in 1:1.5 ratios against dopaminergic-D$_2$, and serotonergic (5HT$_{2A}$) receptors (in vitro) and amphetamine induced hyperactive mouse model (in vivo). Isolation of α-yohimbine, reserpiline and a mixture of 10-demethoxyreserpiline and 11-demethoxyreserpiline in 1:1.5 ratios were carried out from the leaves of R. tetraphylla.

Earlier the major thrust of antipsychotic drugs development was centered around the dopamine since all antipsychotic drugs potently block dopamine receptors, but in the recent past more attention has been focused on serotonin 5-HT$_{2A}$ and 5-HT receptors as atypical antipsychotic drugs (e.g. clozapine, olanzepine, and risperidone) potently block these receptors.

It has been common observation that herbal formulations are better than the synthetic drugs as they do not possess serious side effects and chronic toxicity. So in order to find out more potent antipsychotic plant product or herbal formulation, we carried out a systematic bioactivity guided fractionation and isolation of antipsychotic compounds from the leaves of an Indian medicinal plant R. tetraphylla. The subject mentioned below specially describes the manner in which the antipsychotic extracts and compounds were obtained.

OBJECTIVES OF THE PRESENT INVENTION

The main object of the present invention is to develop novel non toxic antipsychotic agents without any extra pyramidal symptoms for the treatment of psychosis.

Another object of the invention is to provide standardized antipsychotic herbal extracts and its bioactive fractions from the leaves of R. tetraphylla.

Another object of the invention is to provide an herbal formulation comprising antipsychotic extract and its bioactive fractions obtained from the leaves of R. tetraphylla.

Still another object of the invention is to provide a process for the preparation antipsychotic extracts from the leaves of R. tetraphylla.

Still another object of the present invention is to isolate, characterize and establish nature of the antipsychotic compounds from the active leaf extract R. tetraphylla.

Still another object of the invention is to test the antipsychotic potential of isolated biomolecules from the leaves of R. tetraphylla using in-vitro and in-vivo assays to identify the mechanism of action.

BRIEF DESCRIPTION OF THE DRAWINGS

FIG. 8: various steps for extractions and fractions of methanol extract FIG. 9: schematic isolation procedure of antipsychotic compound from the ethylacetate fraction FIG. 10. schematic procedure pH-Gradient fractionation and alkaloid extractions from the methanol extract FIG. 11: schematic isolation procedure of antipsychotic compounds from the CHCl$_3$ extract

SUMMARY OF THE INVENTION

Figure 1:
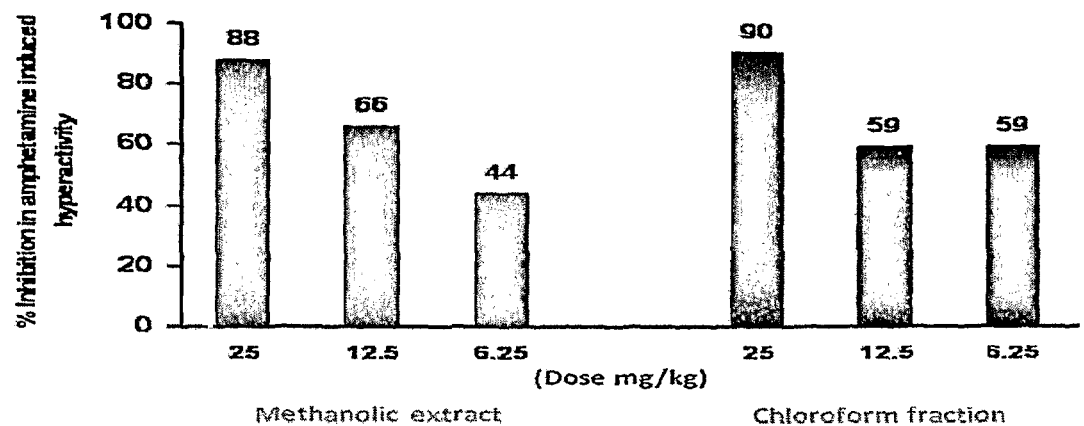
FIG. 1: Antipsychotic activity evaluation of methanolic extract (1A) and chloroform fraction (2C) of *Rauwolfia tetraphylla* leaves on mouse model

Accordingly, the present invention provides bioactive fractions obtained from plant *Rauwolfia*, wherein the said fractions comprising the compounds
 (a) Isoreserpiline ranging between 13 to 22%;
 (b) Reserpiline ranging between 15 to 43%;
 (c) 11-Demethoxy reserpiline and 10-Demethoxy reserpiline ranging between 1 to 15%;

(d) 10-Methoxytetrahydroalstonine ranging between 3 to 22%;
(e) α-Yohimbine ranging between 10 to 39%;
(f) unidentified components ranging between 1 to 20%.

In another embodiment of the present invention the alcoholic extract (1A) forming the bioactive fraction comprising α-yohimbine ranging from 35 to 39, isoreserpiline ranging from 18 to 22, reserpiline ranging from 15 to 19, 10-methoxytetrahydroalstonine ranging from 18 to 22, 10-demethoxyreserpiline and 11-demethoxyreserpiline ranging 1 to 5% and unidentified constituents ranging from 1 to 5%.

In another embodiment of the present invention the alcoholic extract forming the ethyl acetate fraction (1C) comprising α-yohimbine ranging from 17 to 21, isoreserpiline ranging from 13 to 17, reserpiline ranging from 28 to 32, 10-methoxytetrahydroalstonine ranging from 3 to 8, 10-demethoxyreserpiline and 11-demethoxyreserpiline ranging from 11 to 15% and unidentified constituents ranging from 10 to 20%.

In yet another embodiment of the present invention the alcoholic extract forming the chloroform fraction (2C) comprising the α-yohimbine ranging from 10 to 15, isoreserpiline ranging from 14 to 18, reserpiline ranging from 39 to 43, 10-methoxytetrahydroalstonine ranging from 9 to 14, 10-demethoxyreserpiline and 11-demethoxyreserpiline ranging from 7 to 12% and unidentified constituents ranging from 5 to 15%.

In yet another embodiment of the invention the % age of compounds is based on relative area count % obtained in HPLC fingerprint.

In another embodiment of the invention the compounds (c) and (d) are represented by the general formula 1,

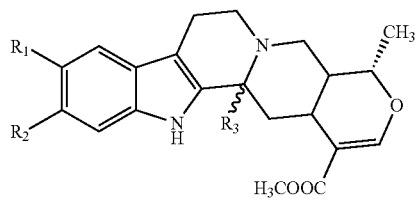

Formula 1 wherein,
R1=OMe R$_2$=H R$_3$=β-H (11-Demethoxy reserpiline),
R$_1$=H R$_2$=OMe R$_3$=β-H (10-Demethoxy reserpiline),
R$_1$=OMe R$_2$=H R$_3$=α-H (10-Methoxytetrahydroalstonine)

Another embodiment of the invention the alcoholic extract obtained from the leaves of the plants of genus *Rauwolfia* is selected from a group consisting of *R. serpentina, R. canesceus, R. vomitoria, R. tetraphylla*.

In another embodiment of the invention a process for preparation of bioactive extract, its fractions and isolation of compounds the process steps comprising;
(a) powdering the plant part of *Rauwolfia*;
(b) extracting the plant powder of step (a) by soaking in a low molecular weight alcohol for a period of 16-20 hours;
(c) filtering the alcoholic extract of step (b);
(d) evaporating the solvent of step (c) under reduced pressure to obtain an alcoholic extract (1A);
(e) testing bioactivity and toxicity of alcoholic extract to identify alcoholic extract as a non toxic, antipsychotic extract;
(f) extracting the alcoholic extract of step (d) with 2-5% aqueous acidic solution;
(g) defatted the acidic solution of step (f) with an organic solvent;
(h) basifying the defatted acidic extract of step (g) at temperature ranging from 3 to 8° C.;
(i) extracting the basified extract of step (h) with a medium polarity organic solvent;
(j) washing the combined organic extract obtained in step (i) with water, drying over anhydrous sodium sulphate and removing the solvent under vacuum to obtain alkaloid fraction (2C);
(k) purifying the alkaloid fraction as obtained from step (j) by using flash chromatography;
(l) eluting FC column of alkaloid fraction as obtained from step (j) with hexane:EtOAc (3:1) to isolate tetrahydroalstonin (K006) and 10-methoxytetrahydroalstonin (K003) from fractions 8-12 and 13-15, Isoreserpiline (K005) from fractions 17-21, isomeric mixture of 10-demethoxyreserpiline and 11-demethoxyreserpiline (K004) from fractions 66-81, α-Yohimbine (K001) from fractions 98-129 and reserpiline (K002) from fractions 137-168, respectively;
(m) antipsychotic fraction of step (j) can also be obtained by dissolving the alcoholic extract obtained in step (d) in distilled water;
(n) filtering the aqueous solution of step (m);
(o) extracting the aqueous solution of step (n) successively with hexane, ethyl acetate, and finally with n-butanol to obtain respective organic fractions and an aqueous fraction;
(p) washing the combined hexane and ethyl acetate fractions of step (o) separately with a small amount of water and drying over anhydrous sodium sulphate;
(q) distilling off solvents hexane and ethyl acetate of step (o) and butanol and aqueous fraction of step (x) separately under vacuum to respectively obtain residues of hexane (1B), ethyl acetate (1C), butanol (ID) and aqueous fractions (1E);
(r) testing the bioactivity of various residues obtained;
(s) isolating the α-Yohimbine (K001) from the ethyl acetate (1C) fraction, obtained in step (q) using chromatographic methods using hexane:EtOAc 1:1, Hexane: EtOAc 65:35, Hexane: EtOAc 70:30 and t BuMe ether: ACN:water+0.8 mM TFA 4:1:5.

Yet another embodiment of the invention the low molecular weight alcohol is selected from the group of methanol or ethanol.

Yet another embodiment of the invention the extraction of plant material can also be achieved within the time period of 3-5 hours using continuous hot soxhlet extraction.

Yet another embodiment of the invention the acid used is selected from a group consisting of acetic acid, citric acid, tartaric acid, HCl, $H_2SO_4$, $H_3PO_4$, and $HNO_3$, preferably HCl.

Yet another embodiment of the invention the organic solvent used for defattening of acid extract is selected from a group consisting of petroleum ether, hexane, dichloromethane, chloroform, ethyl acetate and diethyl ether, preferably hexane.

Another embodiment of the invention the basifying agent is selected from a group consisting of ammonia solution, sodium bicarbonate, sodium carbonate, sodium hydroxide and potassium hydroxide, preferably sodium carbonate.

Another embodiment of the invention the pH of basified extract is kept between 8-12, preferably 9.

Another embodiment of the invention the medium polarity organic solvent used is selected from a group consisting of dichloromethane, chloroform, ethyl acetate and diethyl ether, preferably chloroform.

Another embodiment of the invention the alcoholic extract of *Rauwolfia tetraphylla* leaves showed potential antipsychotic activity without any extra pyramidal symptoms (EPS) and toxicity.

Another embodiment of the invention the extract and its fractions are useful for the treatment of psychosis and showed 33-90% inhibition in amphetamine induced hyperactivity mice model.

Yet another embodiment of the invention the extract and its fractions showed binding inhibition to dopamine and serotonin receptors whose IC 50 values ranges between 2.42 to 12.73.

Yet another embodiment of the invention the α-yohimbine at 6.25 mg/Kg showed >60% inhibition in amphetamine induced hyperactivity mice model.

In yet another embodiment of the invention a compound of general formula 1a and isomers thereof comprising;

General formula 1a

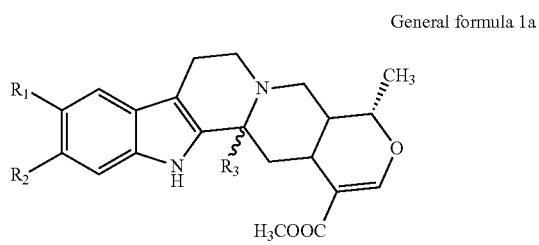

wherein $R_1$=OMe $R_2$=H $R_3$=β-H (11-Demethoxy reserpiline)

$R_1$=H $R_2$=OMe $R_3$=β-H (10-Demethoxy reserpiline)

$R_1$=OMe $R_2$=H $R_3$=α-H (10-Methoxytetrahydroalstonine)

Yet another embodiment of the invention the use of the compounds for the treatment of psychotic conditions in a subject the general formula 1 and formula 2 comprising;

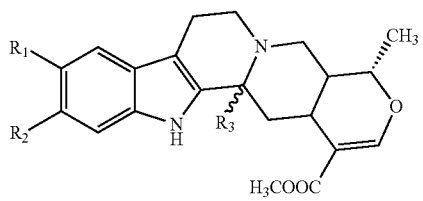

1. $R_1$ = $R_2$ = OMe $R_3$ = α-H (Isoreserpiline)
2. $R_1$ = $R_2$ = OMe $R_3$ = β-H (Reserpiline)
3. $R_1$ = OMe $R_2$ = H $R_3$ = β-H (11-Demethoxy reserpiline)
4. $R_1$ = H $R_2$ = OMe $R_3$ = β-H (10-Demethoxy reserpiline)
5. $R_1$ = $R_2$ = H $R_3$ = α-H (Tetrahydroalstonine)
6. $R_1$ = OMe $R_2$ = H $R_3$ = α-H (10-Methoxytetrahydroalstonine)

Formula-2

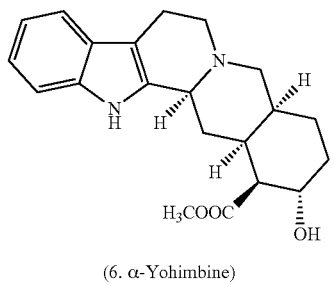

(6. α-Yohimbine)

Another embodiment of the invention the dosage of compounds of general formula 1 and 2 is ranging between 6.25 to 25 mg/Kg body weight on mice.

Another embodiment of the invention the α-yohimbine at 6.25 mg/Kg showed >60% inhibition in amphetamine induced hyperactivity mice model.

Another embodiment of the invention the ratio of 10-demethoxyreserpiline and 11-demethoxyreserpiline is 1:1.5

Yet another embodiment of the invention an effective dose of bioactive extract or its fractions or any of the compound of general formula 1 and 2 individually or in combination thereof optionally along with a pharmaceutically acceptable additives carriers, diluents, solvent, filter, lubricant, excipient, binder or stabilizer.

DETAILED DESCRIPTION OF INVENTION

In our efforts to discover new antipsychotics from plant sources, we found that the methanolic extract of *R. tetraphylla* leaves showed significant antipsychotic activity against dopaminergic-$D_2$ and Serotonergic ($5HT_{2A}$) receptors in vitro and amphetamine induced hyperactive mouse model in vivo. The active methanolic extract of the leaves was then subjected to bioactivity guided fractionation and the antipsychotic chloroform extract resulted in the isolation of six pure compounds, which were characterized on the basis of their spectroscopic data as α-yohimbine, reserpiline, tetrahydroalstonine, 10-methoxytetrahydroalstonine, isoreserpiline, a mixture 10-demethoxyreserpiline and 11-demethoxyreserpiline (in 1:1.5 ratios). All the isolated compounds showed varying degree of antipsychotic activity against dopaminergic-$D_2$ and Serotonergic ($5HT_{2A}$) receptors in-vitro and amphetamine induced hyperactive mouse model in-vivo. *R. tetraphylla* is an important medicinal plant having wide distribution in India, Australia tropical South America and the Caribbean. The plant is important because of the presence of bioactive alkaloids in its roots. Although several alkaloids have been reported from the leaves of this plant but to the best of our knowledge no antipsychotic activity has been reported in any of the extracts or in the isolated molecules so far.

The present invention provides a pharmaceutical composition comprising an effective amount of an antipsychotic extract or α-yohimbine, reserpiline or a mixture 10-demethoxyreserpiline and 11-demethoxyreserpiline in 1:1.5 ratios along with pharmaceutically acceptable additives for the treatment of psychosis in human without any extra pyramidal symptoms (EPS).

Recently MeOH extract of *R. tetraphylla* leaves has shown potential in-vivo antipsychotic activity in our hand as shown below in Table 1.

TABLE 1

Antipsychotic activity of MeOH extracts of *Rauwolfia tetraphylla* leaves

| Extract/compound I.D. | Dose (mg/Kg) | Activity |
|---|---|---|
| Methanol extract | 25 | 78% |
| Reserpine | 2.5 | 16% |

It is interesting to note that this antipsychotic activity in the leaves *R. tetraphylla* was not attributed due to reserpine, which is explained as given below.

1. HPLC analysis of *R. tetraphylla* dry leaves showed us that it contained almost negligible amount 0.0092% of reserpine. Therefore, the administered dose (25 mg) of the MeOH extract will not contain biologically effective concentration of reserpine, which is explained below.

100 g of dry leaves of *Rauwolfia tetraphylla* gave us 22.1 g of MeOH extract of which 25 mg (or 0.025 g) dose in the above table showed 78% antipsychotic activity. Hence the amount of reserpine in 25 mg of MeOH extract can be calculated as shown below. Since 22.1 g of MeOH extract (obtained from 100 g of dry leaves) contain 0.0092 g of reserpine Hence 0.025 g (25 mg) of MeOH extract will contain $$\frac{0.0092 \times 0.025}{22.1} = 0.00001041 \text{ g or } 0.01041 \text{ mg of reserpine}$$

From the above it is evident that 0.01 mg of reserpine present in 25 mg of MeOH extract in the above Table 1 can not impart such a potential antipsychotic activity.

Further MeOH extract of *R. tetraphylla* leaves was found to be significantly active on dopamine-D2 and serotonine-2A receptors as revealed by its activity on the binding of 3H-spiperone to striatal and 3H-Ketanserin to frontocortical membranes respectively. Since, reserpine is a depletor and does not bind to the above receptors, confirming that the potential antipsychotic activity of the MeOH extract on the receptor binding is not due to reserpine but is due to presence of other bioactive substances in the leaves.

The methodology followed by us for the preparation of standardized extracts and activity guided fractionation, isolation and characterization of antipsychotic agents from *R. tetraphylla* and their in-vitro and in-vivo antipsychotic screening has been described below as examples.

Following examples are given by way of illustrations and should not construed the scope of the present invention.

Example-1

Collection of Plant Material and Extraction

The leaves of *R. tetraphylla* were collected from our research farm in Lucknow, India, in the month of January 2007. The finely crushed leaves were successively extracted thrice at room temperature over night with methanol in a percolator. The combined methanol extract was concentrated under vacuum on a BuchiRotavapor and finally dried on a high vacuum pump until the methanol was completely removed. The MeOH extract was evaluated for its antipsychotic activity and the results are shown above in Table-1

Example-2

Fractionation of Methanol Extract and Antipsychotic Activity Evaluation of Various Fractions The leaves of *Rauwolfia tetraphylla* were shade dried. The dried leaves were powdered (190 g) and extracted overnight with methanol at room temperature. This extraction process was repeated four times. The combined methanol extract was dried under vacuum which yielded crude MeOH extract (42 g). The methanol extract was further dissolved in distilled water and subsequently extracted four times with hexane, EtOAc and BuOH (saturated with water). The combined hexane and EtOAc extracts were washed with water, dried over anhydrous sodium sulphate and solvent removed under vacuum to yield hexane and EtOAc extracts. The BuOH extract was distilled by adding distill water in to BuOH extract time to time. The various extractions and fractions steps are shown in FIG. 8 i.e. flow chart 1.

The above fractions were evaluated for their antipsychotic activity. In order to assess the antipsychotic potential of MeOH extract, its various fractions, alkaloids isolated and their derivatives from *Rauwolfia tetraphylla* leaf, amphetamine induced hyper activity mouse model was used following the method of Szewczak et al (1987). Adult Swiss mice of either sex (25±2 g body weight) obtained from the Indian Institute of Toxicology Research (IITR), Lucknow, India animal-breeding colony were used throughout the experiment. The animals were housed in plastic polypropylene cages under standard animal house conditions with a 12 hours light/dark cycle and temperature of 25±2° C. The animals had adlibitum access to drinking water and pellet diet (Hindustan Lever Laboratory Animal Feed, Kolkata, India). The Animal Care and Ethics Committee of IITR approved all experimental protocols applied to animals. The results are shown in Table 2

TABLE 2

Antipsychotic activity evaluation of various extracts and fractions of *Rauwolfia tetraphylla* leaves on amphetamine induced mouse model

| Extract/ fraction I.D. | Dose (mg/Kg) | Distance traveled (cm) | Anti-psychotic activity (% inhibition in amphetamine induced hyper-activity) |
|---|---|---|---|
| Control | — | — | — |
| Amphetamine (Amph) | 5 | 6064 | — |
| Methanol extract (1A) + Amph | 50 | 606 | 90 |
|  | 25 | 1334 | 78 |
| Hexane fraction (1B) + Amph | 25 | 1819 | 70 |
| EtOAc fraction (1C) + Amph | 25 | 667 | 89 |
| BuOH fraction (1D) + Amph | 25 | 2001 | 67 |
| Aqueous fraction (1E) + Amph | 25 | 1879 | 69 |
| Reserpine | 5 | 4002 | 34 |
| Reserpine | 2.5 | 5093 | 16 |

Values are mean of 6 mice in each group.
Amph stands for amphetamine.

Mice were injected with amphetamine (5 mg/kg, i.p.) 60 minutes after oral treatment with respective extract in each group. From the Table 2, it is evident that EtOAc fraction (1C) was most active followed by methanol extract (1A), hexane (1B) Aqueous (1E) and BuOH (1D) fractions respectively.

Example-3

Isolation of Antipsychotic Compound from the Ethylacetate Fraction of *Rauwolfia tetraphylla* Leaves Isolation of antipsychotic compounds from the ethylacetate extract (1C) of Example 2 was carried out by Vacuum Liquid Chromatography (VLC). VLC column was packed with TLC grade silica (silica gel H, 210 g) in a 500 ml capacity sintered funnel (G1, 115×110 mm). EtOAc extract (43 g) was dissolved in minimum amount of MeOH and loaded on the top of VLC column in usual way. The column was dried under vacuum for 15 minutes to remove the polar solvent. Fraction of 500 ml each was collected. Elution of the VLC column was carried out with mixture of solvents: hexane, EtOAc and methanol in increasing order of polarity. A total of 174 fractions were collected. Fractions 18-26 (5.2 g) eluted with hexane:EtOAc (1:1) were further separated on silica gel (60-120 mesh, 150 g) column. Fraction of 100 ml each was collected. Elution of the column was carried out with mixture of solvents: hexane, EtOAc and methanol in increasing order of polarity. A total of 305 fractions were collected. Fractions 189-206 eluted with hexane: EtOAc (65:35) resulted in the isolation of α-Yohimbine (K001) (15 mg). Further fractions 170-179, 182-183, 186, 207-217 eluted with hexane:EtOAc (70:30) were polled (800 mg) together on the basis of their TLC profile and further separated by Flash Chromatography using TLC grade silica (silica gel H, 30 g). Elution of the column was carried out with mixture of solvents: hexane, EtOAc and methanol in increasing order of polarity. Fractions of 50 ml each were collected. A total of 156 fractions were collected. Fractions 33-43 (416 mg) eluted with hexane:EtOAc (70:30) were further separated by Fast Centrifugal Partition Chromatography (FCPC) using solvent system: t BuMe ether: ACN:water+0.8 mM TFA 4:1:5. Aqueous layer was made as stationary phase and organic layer made as mobile phase. Fractions of 15-20 ml were collected. A total of 23 fractions were collected. Fractions 19-20 were homogeneous on TLC and characterized as α-Yohimbine (40.3 mg). A schematic isolation procedure is given in FIG. 9 i.e. flow chart 2

Example-4 pH-Gradient Fractionation of Alkaloids from the Methanol Extract of *Rauwolfia tetraphylla* Leaves and Antipsychotic Activity Evaluation of Various Fractions The dried leaves were powdered (190 g) and extracted overnight with methanol at room temperature. This extraction process was repeated four times. The combined methanol extract was dried under vacuum which yielded crude MeOH extract (42 g). The methanol extract was extracted 20 times with 150 ml of 2% HCl solution. The combined Acidic extract was successively defatted four times with hexane and $CHCl_3$. The combined hexane, $CHCl_3$ extracts were washed with water, dried over anhydrous sodium sulphate and solvent removed under vacuum to yield hexane (2A), $CHCl_3$ (2B) extracts. The acidic extract was then basified in cold with $Na_2CO_3$ up to pH-9 and extracted with $CHCl_3$ 5-7 times. The aqueous basic extract (pH-9) was further basified in cold with 5% NaOH solution and extracted with $CHCl_3$. The combined $CHCl_3$ extracts at pH 9 and 12 were separately washed with water, dried over anhydrous sodium sulphate and solvent removed under vacuum to yield $CHCl_3$ extracts at pH 9 (2C) and 12 (2D). Finally the aqueous basic extract (pH-12) was neutralized and distilled by adding n-BuOH in to aqueous extract from time to time. The alkaloid extractions and pH gradient fraction steps are shown in the FIG. 10, i.e. flow chart 3.

All the above fractions were evaluated for their antipsychotic activity and the results are presented below in Table 3

TABLE 3

Antipsychotic activity evaluation of various alkaloid extract of *Rauwolfia tetraphylla* leaves on amphetamine induced mouse model

| Extract/ fraction I.D. | Dose (mg/Kg) | Distance traveled (cm) | Anti-psychotic activity (% inhibition in amphetamine induced hyperactivity) |
|---|---|---|---|
| Control | — | — | — |
| Amphetamine (Amph) | 5 | 6064 | — |
| Methanol extract (1A) + Amph | 50 | 606 | 90 |
|  | 25 | 1334 | 78 |
| $CHCl_3$ fraction at pH 2 (2B) + Amph | 25 | 2061 | 66 |
| $CHCl_3$ fraction at pH 9 (2C) + Amph | 25 | 667 | 89 |
| $CHCl_3$ fraction at pH 12 (2D) + Amph | 25 | 2489 | 59 |
| Aqueous fraction (2E) + Amph | 25 | 4062 | 33 |
| Reserpine | 5 | 4002 | 34 |
| Reserpine | 2.5 | 5093 | 16 |

Values are mean of 6 mice in each group.
Amph stands for amphetamine.
Mice were injected with amphetamine (5 mg/kg, i.p.) 60 minutes after oral treatment with respective extract in each group.

From the Table 3, it is evident that $CHCl_3$ fraction at pH 9 (2C) was most active followed by methanol extract (1A), $CHCl_3$ fraction at pH 2 (2B), $CHCl_3$ fraction at pH 12 (2D) and aqueous fraction (2E) respectively.

Methanol extract (1A) and Chloroform extract (2C) were further tested for their antipsychotic potentials at lower doses and the results are shown below in FIG. 1.

Values are mean of five animals in each group
% Inhibition calculated with respect to amphetamine induced hyperactivity
No EPS observed at any of the dose

Example-5

Isolation of Antipsychotic Compounds from the Alkaloid Fraction (2C) of *Rauwolfia tetraphylla* Leaves $CHCl_3$ extract (2C) at pH-9 was subjected for HPLC analysis. HPLC analysis was performed on a Shimadzu (Tokyo, Japan) model LC-10A instrument equipped with a Shimadzu SPD-M10A$_{VP}$ Photodiode array detector (PDA) in order to determine peak purity and similarity test of methanol extract. HPLC grade solvents (Merck, Darmstadt, Germany) were prefiltered using a Millipore (Billerica, Mass., USA) system and analysis was performed on a waters (Milford, Mass., USA) $C_{18}$spherisorb S10 $ODS_2$ (250×4.6 mm i.d., 10 μm) column. The mobile phase was acetonitrile: acidified water containing 1% TFA (70:30) at a flow rate of 1 ml/min. The detection wavelength was 220 nm.

Figure 2:
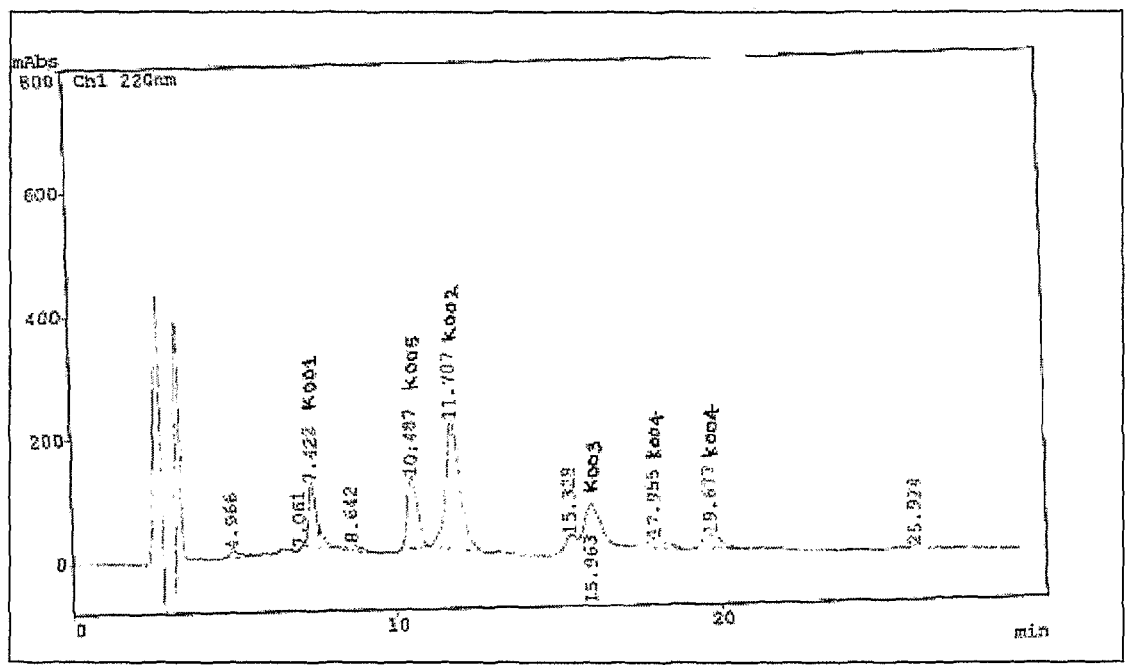
FIG. 2: HPLC profile of CHCl$_3$ extract (2C)
Figure 3:
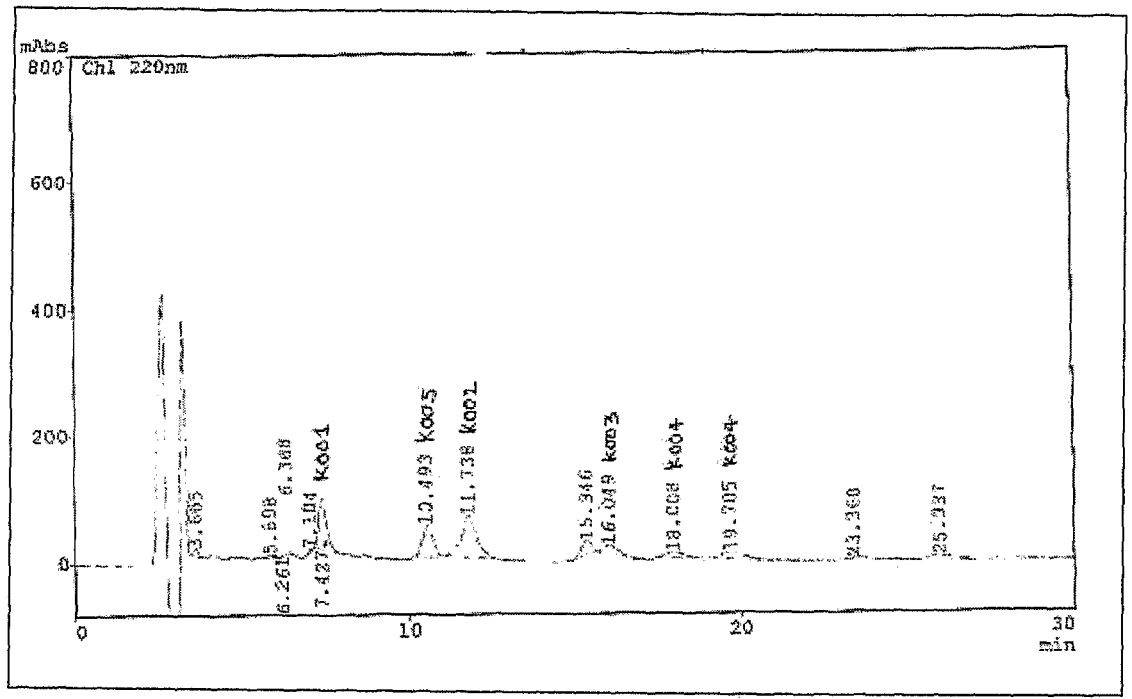
FIG. 3: HPLC profile of EtOAc extract (1C)
Figure 4:
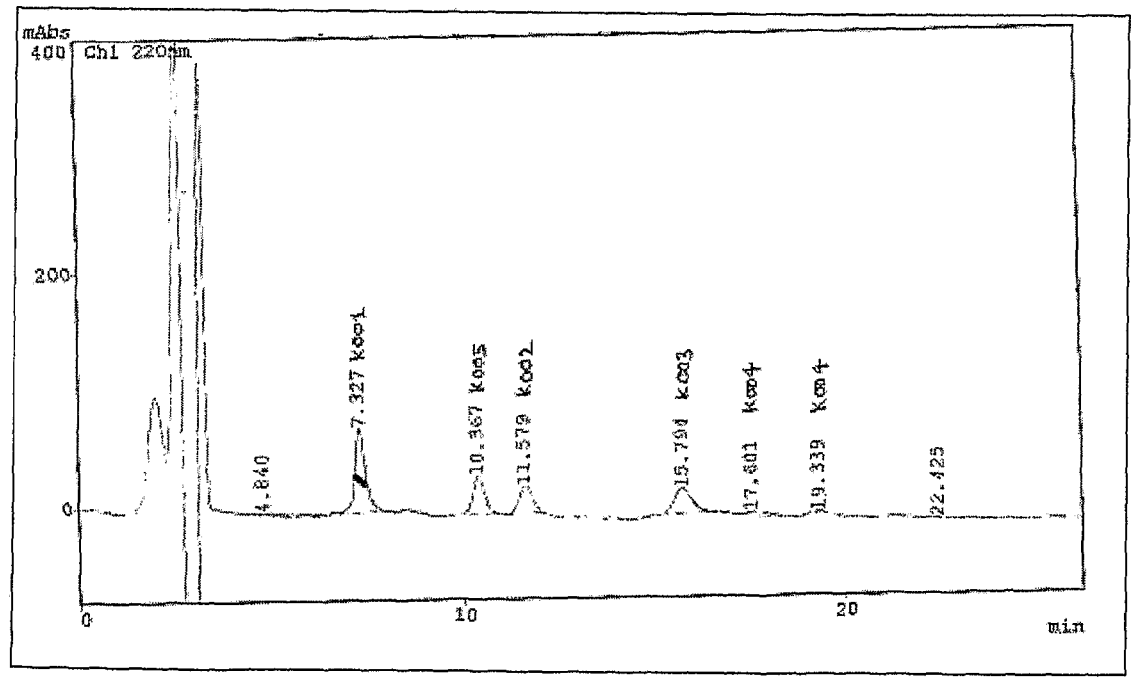
FIG. 4: HPLC profile of MeOH extract (1A)

The HPLC profile of $CHCl_3$ extract (2C), EtOAc (1C) and MeOH (1A) are presented in FIG. 2, FIG. 3 and FIG. 4 and the data obtained from HPLC are presented in table-4, table-5 and table-6:

TABLE 4

HPLC profile data from Chloroform Extract (2C)

* Peak Report *

| PKNO | ChNO | TIME | AREA | MK | PURITY.UP | PURITY.DOWN | IDNO | CONC |
|---|---|---|---|---|---|---|---|---|
| 1 | 1 | 4.966 | 270067 | | | | | 1.8120 |
| 2 | 1 | 7.061 | 2936 | | | | | 0.0197 |
| 3 | 1 | 7.422 | 1897902 | | | | | 12.7339 |
| 4 | 1 | 8.642 | 276499 | | | | | 1.8552 |
| 5 | 1 | 10.487 | 2431062 | | | | | 16.3112 |
| 6 | 1 | 11.707 | 6179114 | | | | | 41.4587 |
| 7 | 1 | 15.328 | 267125 | | | | | 1.7923 |
| 8 | 1 | 15.963 | 1746381 | | | | | 11.7173 |
| 9 | 1 | 17.936 | 550440 | | | | | 3.6932 |
| 10 | 1 | 19.677 | 877429 | | | | | 5.8871 |
| 11 | 1 | 25.924 | 405318 | | | | | 2.1195 |
| | | | 14904273 | | | | | 100.000 |

TABLE 5

HPLC profile data from Ethyl acetate Extract (1C)

* Peak Report *

| PKNO | ChNO | TIME | AREA | MK | PURITY.UP | PURITY.DOWN | IDNO | CONC |
|---|---|---|---|---|---|---|---|---|
| 1 | 1 | 3.665 | 91049 | | | | | 1.3415 |
| 2 | 1 | 5.898 | 51480 | | | | | 0.7585 |
| 3 | 1 | 6.261 | 3507 | | | | | 0.0517 |
| 4 | 1 | 6.368 | 1272 | | | | | 0.0187 |
| 5 | 1 | 7.104 | 32721 | | | | | 0.4821 |
| 6 | 1 | 7.427 | 1310455 | | | | | 19.3075 |
| 7 | 1 | 10.493 | 1013495 | | | | | 14.9323 |
| 8 | 1 | 11.738 | 2074985 | | | | | 30.5717 |
| 9 | 1 | 15.346 | 515824 | | | | | 7.5999 |
| 10 | 1 | 16.049 | 383734 | | | | | 5.6537 |
| 11 | 1 | 18.008 | 409848 | | | | | 6.0385 |
| 12 | 1 | 19.705 | 510032 | | | | | 7.5145 |
| 13 | 1 | 23.360 | 2389 | | | | | 0.0352 |
| 14 | 1 | 25.937 | 386483 | | | | | 5.6942 |
| | | | 6787273 | | | | | 100.0000 |

TABLE 6

HPLC profile data from methanol extract (1A)

* Peak Report *

| PKNO | ChNO | TIME | AREA | MK | PURITY.UP | PURITY.DOWN | IDNO | CONC |
|---|---|---|---|---|---|---|---|---|
| 1 | 1 | 4.840 | 62958 | | | | | 1.7764 |
| 2 | 1 | 7.327 | 1320250 | | | | | 37.2513 |
| 3 | 1 | 10.367 | 721658 | | | | | 20.3618 |
| 4 | 1 | 11.579 | 596457 | | | | | 16.8292 |
| 5 | 1 | 15.794 | 719119 | | | | | 20.2902 |
| 6 | 1 | 17.601 | 111380 | | | | | 3.1426 |
| 7 | 1 | 19.339 | 6929 | | | | | 0.1955 |
| 8 | 1 | 22.425 | 5426 | | | | | 0.1531 |
| | | | 3544176 | | | | | 100.0000 |

Isolation of antipsychotic compounds from the CHCl$_3$ extract (2C) of Example 4 was carried out by Flash Chromatography (FC). FC column was packed with TLC grade silica (silica gel H, 20 g). CHCl$_3$ extract (2C, 2.67 g) was dissolved in minimum amount of MeOH and loaded on the top of FC column in usual way. The column was dried under vacuum for 15 minutes to remove the polar solvent. Fractions of 50 ml each were collected. Elution of the FC column was carried out with mixture of solvents: hexane, EtOAc and methanol in increasing order of polarity. A total of 186 fractions were collected. Fractions 3-132 were eluted with hexane:EtOAc (3:1). Fractions 8-12 were further separated on silica gel (60-120 mesh, 10 g) column. Elution of the column was carried out with mixture of hexane and EtOAc in increasing order of polarity. Fractions 8-12 eluted with hexane:EtOAc (9:1) resulted in the isolation of Tetrahydroalstonin (K006), while the fraction 19-24 eluted with hexane:EtOAc (9:1) resulted in the isolation of 10-Methoxytetrahydroalstonin (K003). Further fractions 13-15 of flash chromatography also resulted in the isolation of 10-Methoxytetrahydroalstonin (K003), while fractions 17-21 resulted in the isolation of Isoreserpiline (K005). On the other hand FC fractions 66-81 were characterized as an isomeric mixture of 10-Demethoxyreserpiline and 11-Demethoxyreserpiline (K004). Similarly FC fraction 98-129 resulted in the isolation of α-Yohimbine (K001, 120 mg). FC fractions 137-168 eluted with hexane: EtOAc (6:4 and 4:6) resulted in the isolation of reserpiline (K002, 134.8 mg). A schematic isolation procedure of antipsychotic compounds from the $CHCl_3$ extract (2C) of Example 4 is given in FIG. 11 i.e. flow chart 4.

Chromatographic separation resulted in the isolation of six compounds. The compound K004 was an isomeric mixture of two compounds, 10-Demethoxyreserpiline and 11-Demethoxyreserpiline. In this way from the $CHCl_3$ extract (2C) of Example 4 a total of six compounds were isolated but seven compounds were characterized.

Characterization of Antipsychotic Alkaloids from *R. tetraphylla*

10-methoxy tetrahydroalstonine (K003):

Compound K003 was isolated as light reddish, amorphous solid with the molecular formula of $C_{22}H_{26}N_2O_4$ (m/z 382), ES1MS (−) 381, (+) 383. The $^{13}$C NMR ($CDCl_3$, 75 MHz) and HSQC data showed the presence of 3 methyl, 4-methylene, 8 methine and 7 quaternary carbon atoms in the molecule. The $^1$H NMR spectrum ($CDCl_3$, 300 MHz) accounted for all 26 protons. The $^1$H and $^{13}$C NMR spectrum of K003 closely resembled to tetrahydroalstonine [Janot et al, Helv. Chim Acta 34, 1207, 1951, Wenkert et al, J. Am. Chem. Soc. 98, 3645, 1976]. Further, apart from signals for tetrahydroalstonine, K003 showed an additional signal at δ 3.84 (3H,$) in $^1$H and at 154.6 (C) ppm in $^{13}$C NMR for the presence of a substituted indole moiety and a carbomethoxy group in the aromatic ring. Although, the reported $^{13}$C NMR data for 11-methoxytetrahydroalstonine [Mukhopadhyay et al, Phytochemisrty 30(7), 2447, 1991] did not match with those of K003 but the appearance of the C-9 and C-11 methine carbon signals at a reasonably upfield positions [101.4 ppm (C-9), 111.4 ppm (C-11)] in K003 relative to that in tetrahydroalstonine [117.9 (c-9), 121.1 (c-11)] immediately settled the location of the methoxyl group at C-10. Further a quaternary carbon at 154.6 ppm showing HMBC cross peaks from H-9, H-11, H-12 and OMe (δ 3.84) was assigned to C-10. Further conformation of methoxy group at C-10 was made from the reported $^{13}$C NMR data of ring A for 17-hydroxy-10-methoxy-yohimbane (Salim et al J. Nat. Prod. 67, 1719, 2004). The relative stereochemistry of K003 was determined by comparison of the $^{13}$C NMR spectra with literature data. Comparison of $^{13}$C NMR data with the series of yohimbinoids described by Wenkert et. al. (J. Am. Chem Soc. 1976, 98, 3645-3655) showed that KOO3 has the same stereochemistry as yohimbine at the asymmetric centers C-3, C-15 and C-20. The coupling constants of H-14β (J=12.3, 12.3, 12.0 Hz) were consistent with trans-diaxial relationship to both H-3 and H-15. Further the large coupling constant between H-20 and H-21β (J=12.0 Hz) and the appearance of the C-3 methginecorbon signal at 60.4 ppm were consistent with the normal/allo system for the molecule [Janot et al, Helv. Chim Acta 34, 1207, 1951, Wenkert et al, J. Am. Chem. Soc. 98, 3645, 1976, Lounasmaa et al, Tetrahedron, 36, 1607, 1980]. The $^1$H and $^{13}$C NMR spectral data of compound KOO3 with HMBC correlations are shown below.

| # | $^1$H (300 MHz) and $^{13}$C NMR (75 MHz) Spectral data of compound K003 ($CDCl_3$) | | |
|---|---|---|---|
| # | C | H | HMBC Correlations |
| C-2 | 136.7 | | |
| C-3 | 60.4 | 3.34 d (10.8) | C-2 |
| C-5 | 53.9 | 2.50 m α | C-6, C-21, C-3 |
|     |      | 2.90 m β | |
| C-6 | 22.3 | 2.62 m α | C-3, C-5 |
|     |      | 2.93 m β | |
| C-7 | 108.3 | | |
| C-8 | 128.2 | | |
| C-9 | 101.4 | 6.91 d (2.1) | C-7, C-10, C-13, C-11 |
| C-10 | 154.6 | | |
| C-11 | 111.4 | 6.79 dd (8.1, 2.1) | C-9, C-10, C-13 |
| C-12 | 111.8 | 7.12 d (8.7) | C-11, C-10, C-8, C-13 |
| C-13 | 131.9 | | |
| C-14 | 34.8 | 1.50 ddd (12.3, 12.3, 12.0) β | C-15, C-20, C-3 |
|      |      | 2.55 m α | |
| C-15 | 31.9 | 2.75 m | C-14, C-20, C-3, C-19 |
| C-16 | 110.1 | | |
| C-17 | 156.1 | 7.59 s | C-15, C-16, C-19, C-22 |
| C-18 | 18.8 | 1.39 d (6.0) | C-20, C-19 |
| C-19 | 72.9 | 4.49 dq (10.2, 6.0) | C-18, C-15, C-20 |
| C-20 | 39.0 | 1.66 brd (~9.3) | C-21 |
| C-21 | 56.7 | 2.66 m α | C-15, C-20, C-3, C 19, C-5 |
|      |      | 3.06 d (12.0) β | |
| C-22 | 168.4 | | |
| C-23 | 51.3 | 3.75 s | C-22 |
| C-24 | 56.5 | 3.84 s | C-7 |
|      | NH | 8.2 br s | C-7, C-8, C-13, C-2 |

δ values; coupling constants (in Hz) in parontheses

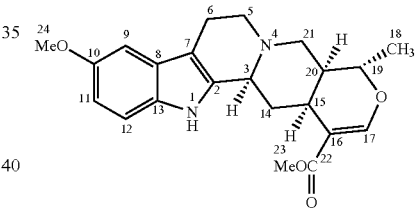

10-methoxytetrahydroalstonine (K003).

Since the new compound KOO3 is a derivative of tetrahydroalstonine and hence named as 10-methoxytetrahydroalstonine on the basis of above spectroscopic data.

10-demethoxyreserpiline and 11-demethoxyreserpiline (K004):

K004 was an isomeric mixture of 10-demethoxyreserpiline and 11-demethoxyreserpiline and was characterized on the basis of its $^{13}$C NMR spectroscopic data.

Characterization of 11-demethoxyreserpiline (K004)

In reserpiline (K002) there are two methoxy groups, each on C-10 and C-11. On comparing the structure of 10-methoxytetrahydroalstonine (K003) with one component, 11-demethoxyreserpiline of K004, one can observe the only difference in the stereochemistry at C-3, which causes characteristic chemical shifts in the carbons of ring C and D. Careful comparison of chemical shifts for the A ring carbons (C-8 to C-13) of 10-methoxytetrahydroalstonine (K003) showed that it completely matches with chemical shifts for the A ring carbons (C-8 to C-13) of 11-demethoxyreserpiline of (K004). The rest of the carbons of ring B, C, D and E were comparable with those for reserpiline [Thesis of M M Queresi; Isolation and structural studies on the chemical constituents of Rhazyastricta, Alstoniamacrophylla and related medicinal plants, 1991, pg: 149, university of Karachi/H.E.J. research institute of chemistry, pakistan (http://docs.google.com/viewer?a=v&q=cache:PyQQgLseE7gJ:prr.hec.gov.pk/Chapters/5710.pdf+M+M+Qureshi%3B+Isolation+and+structural+studies+on+the+chemical+constituents+of+Rhazya+stricta,+Alstonia+macrophylla+and+related+medicinal+plants,+1991&hl=en&gl=in&sig=AHIEtbRepsGEmethEQw9_KLhk0-S1H-3Og)].

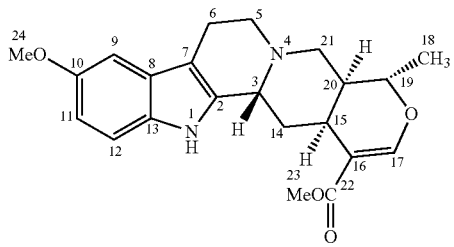

$^{13}$C chemical shift assignments for 11-demethoxyreserpiline (CDCl$_3$)

| C-2 | 131.8 |
|---|---|
| C-3 | 55.03 |
| C-5 | 52.7 |
| C-6 | 19.7 |
| C-7 | 108.1 |
| C-8 | 128.5 |
| C-9 | 101.3 |
| C-10 | 154.7 |
| C-11 | 111.5 |
| C-12 | 111.9 |
| C-13 | 132.6 |
| C-14 | 31.2 |
| C-15 | 26.4 |
| C-16 | 107.6 |
| C-17 | 155.5 |
| C-18 | 18.8 |
| C-19 | 73.8 |
| C-20 | 37.9 |
| C-21 | 52.7 |
| C-22 | 168.1 |
| C-23 | 51.3 |
| C-24 | 56.5 |

Hence on the basis of its $^{13}$C NMR spectroscopic data, one new constituent of K004 was characterized as 11-demethoxyreserpiline.

Characterization of 10-demethoxyreserpiline (K004)

As we discussed above there are two methoxy groups, each on C-10 and C-11 in reserpiline (K002). On comparing the structure of 11-methoxytetrahydroalstonine [Mukhopadhyay et al, Phytochemisrty 30 (7), 2447, 1991] with the other component, 11-demethoxyreserpiline of K004, one can observe the only difference in the stereochemistry at C-3, which causes characteristic chemical shifts in the carbons of ring C and D. Careful comparison of chemical shifts for the A ring carbons (C-8 to C-13) of 11-methoxytetrahydroalstonine showed that it completely matches with the chemical shifts for the A ring carbons (C-8 to C-13) of 11-demethoxyreserpiline (K004). The rest of the carbons of ring B, C, D and E were comparable with those for reserpiline [Thesis of M M Queresi; Isolation and structural studies on the chemical constituents of Rhazyastricta, Alstoniamacrophylla and related medicinal plants, 1991, pg: 149, university of Karachi/H.E.J. research institute of chemistry, pakistan (http://docs.google.com/viewer?a=v&q=cache:PyQQqLseE7gJ:prr.hec.gov.pk/Chapters/5710.pdf+M+M+Qureshi%3B+Isolation+and+structural+studies+on+the+chemical+constituents+of+Rhazya+stricta,+Alstonia+macrophylla+and+related+medicinal+plants,+1991&hl=en&gl=in&sig=AHIEtbRepsGEmethEQw9_KLhk0-S1H-3Og)].

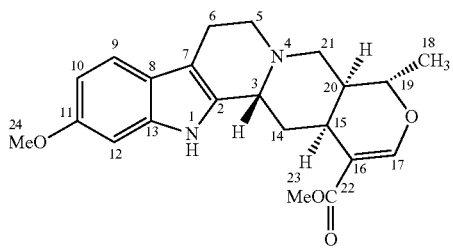

$^{13}$C chemical shift assignments for 10-demethoxyreserpiline (CDCl$_3$)

| C-2 | 131.8 |
|---|---|
| C-3 | 55.1 |
| C-5 | 52.7 |
| C-6 | 19.7 |
| C-7 | 108.1 |
| C-8 | 122.6 |
| C-9 | 118.7 |
| C-10 | 109.4 |
| C-11 | 156.7 |
| C-12 | 95.9 |
| C-13 | 137.3 |
| C-14 | 31.2 |
| C-15 | 26.4 |
| C-16 | 107.6 |
| C-17 | 155.5 |
| C-18 | 18.8 |
| C-19 | 73.8 |
| C-20 | 37.9 |
| C-21 | 52.7 |
| C-22 | 168.1 |
| C-23 | 51.3 |
| C-24 | 56.2 |

Hence on the basis of its $^{13}$C NMR spectroscopic data, the new other constituent of K004 was characterized as 10-demethoxyreserpiline.

Tetrahydroalstonine (K006):

Tetrahydroalstonin was characterized on the basis of its $^{13}$C spectroscopic data with the reported literature data [Pham thanhky et al, Study of Alkaloids from *Uncariasessilifructus* Collected in Cao Bang Province, TC Pharmaceutical materials, 2006, 11 (2), Pg; 60-63.-(Vie).-ISSN 0868-3859]

Isoreserpiline (K005) and reserpiline (K002):

Isoreserpiline and reserpiline were characterized on the basis of their $^{13}$C spectroscopic data with the reported literature data [Thesis of M M Queresi; Isolation and structural studies on the chemical constituents of Rhazyastricta, Alstoniamacrophylla and related medicinal plants, 1991, pg: 149, university of Karachi/H.E.J. research institute of chemistry, pakistan (http://docs.google.com/viewer?a=v&q=cache:PyQQqLseE7gJ:prr.hec.gov.pk/Chapters/5710.pdf+M+M+Qureshi%3B+Isolation+and+structural+studies+on+the+chemical+constituents+of+Rhazya+stricta,+Alstonia+macrophylla+and+related+medicinal+plants,+1991&hl=en&gl=in&sig=AHIEtbRepsGEmethEQw9_KLhk0-S1H-3Og)]

α-Yohimbine (K001):

α-Yohimbine was characterized on the basis of its $^{13}$C spectroscopic data with the reported literature data [Katalin Honty et al, Journal of organic chemistry, 1982, 47, 5111-5114]

Figure 6:
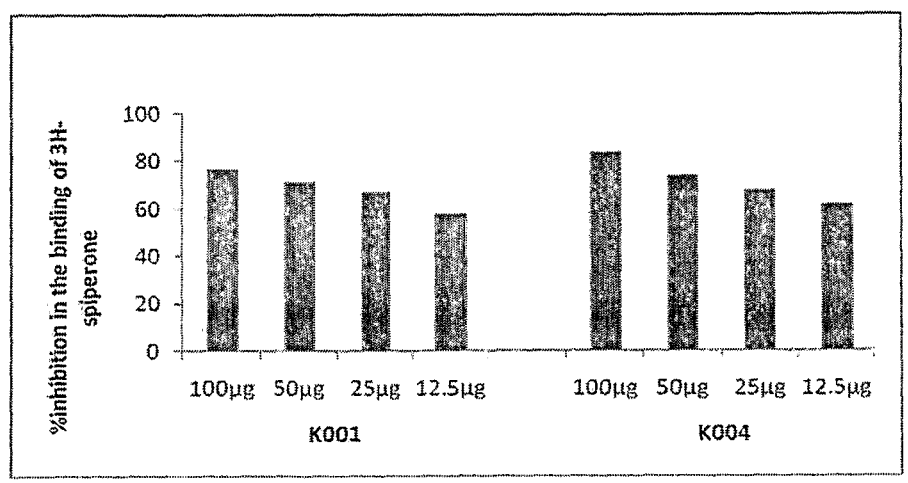
FIG. 6: In-vitro antipsychotic activity of K001 and K004 at lower concentrations

Further these alkaloids were evaluated for their antipsychotic potential on amphitamine induced hyperactive mouse model and the results are shown in FIG. 6.

The isolated compounds K001 and K004 which were showing significant in-vivo antipsychotic activity at lower doses (FIG. 5) were further evaluated for their antipsychotic potential in-vitro at lower doses and the results are presented in FIG. 6.

Compounds, 10-methoxytetrahydroalstonine (K003), 10-demethoxyreserpiline and 11-demethoxyreserpiline (K004) are NEW Compounds and are being Reported for the First Time from Nature.

Antipsychotic activity for all the above compounds [α-yohimbine (K001), reserpiline (K002), 10-methoxytetrahydroalstonine (K003), 10-demethoxyreserpiline and 11-demethoxyreserpiline (K004), isoreserpiline (K005), tetrahydroalstonine (K006)] is being reported for the first time. From the FIG. 5, it is evident that alkaloid α-yohimbine (K001) was more active even at lower doses.

No extra pyramidal symptoms (EPS) were observed for any of the above compounds at any of the above doses.

Standardization of Herbal Extracts and Fractions:

The antipsychotic methanol extract (IA) and EtOAc fraction (1C) and chloroform fraction (2C) were standardized using the isolated marker compounds K001 to K005 HPLC analysis was performed on a Shimadzu (Tokyo, Japan) model LC-10A instrument equipped with a Shimadzu SPD-M10A$_{VP}$ Photodiode array detector (PDA) in order to determine peak purity and similarity test of extract and fractions. HPLC grade solvents (Merck, Darmstadt, Germany) were prefiltered using a Millipore (Billerica, Mass., USA) system and analysis was performed on a waters (Milford, Mass., USA) $C_{18}$spherisorb S10 ODS$_2$ (250×4.6 mm i.d., 10 μm) column. The mobile phase was acetonitrile: acidified water containing 1% TFA (70:30) at a flow rate of 1 ml/min. The detection wavelength was 220 nm.

HPLC fingerprint profile of standardized methanol extract (1A), EtOAc fraction (1C) and chloroform fraction (2C) using the isolated marker compounds K001 to K005 is presented in FIGS. 2-4.

Example-6

In Vitro Antipsychotic Screening

Radioligand Receptor Binding Assay Using Multi Probe II Ex Robotics Liquid Handling System:

Neurotransmitter such as dopamine-D$_2$ and Serotonin (5HT$_{2A}$) are significantly, involved in psychotic behaviour (Creese I, et al., 1976). Hence forth effect of test sample of *Rauwolfia tetraphylla* has been tested on these two receptors using in vitro receptor binding assay with the help of specific radioligand to further support the effect of sample on mouse model.

Using brain region synaptic membrane preparation as source of receptor.

Preparation of Crude Synaptic Membrane:

Rat was killed by decapitation; Brain was removed and dissected the discrete brain regions in cool condition following the standard protocol (Glowinski and Iverson 1966). Crude synaptic membrane from corpus striatum and frontal cortex brain region was prepared separately following the procedure of Khanna et al 1994. Briefly, the brain region was weighed and homogenized in 19 volumes of 5 mM Tris-Hcl buffer (pH 7.4) (5% weight of tissue). The homogenate was centrifuged at 50,000×g for 20 minutes at 4° C. The supernatant was removed and the pellet was dispersed in same buffer pH 7.4, centrifuged at 50,000×g for 20 minutes at 4° C. again. This step help in remaining endogenous neurotransmitter and also help in neuronal cell lyses. The pellet obtained was finally suspended in same volume of 40 mM Tris-Hcl Buffer (pH 7.4) and used as a source of receptor for in vitro receptor binding screening of the samples for Dopaminergic and Serotonergic (5HT$_{2A}$) receptor. Protein estimation was carried out following the method of Lowry et al 1951.

Receptor Binding Assay:

In vitro receptor binding assay for dopamine-D$_2$ and Serotonin (5HT$_{2A}$) was carried out in 96 well multi screen plate (Millipore, USA) using specific radioligands 3H-Spiperone for DAD2 and 3H-Ketanserin for 5HT$_{2A}$ and synaptic membrane prepared from corpus striatal and frontal cortex region of brain as source of receptor detail discussed in table 7 following the method of Khanna et al. (1994)

TABLE 7

Details of radioligands, competitors and brain regions involved in the assay of neurotransmitter receptors.

| Sl. No. | Receptor | Brain Region | Radioligand | Competitor |
|---|---|---|---|---|
| 1. | Dopamine (DA) - D2 | Corpus striatum | $^3$H-Spiperone ($1 \times 10^{-9}$ M) | Haloperidol ($1 \times 10^{-6}$ M) |
| 2. | Serotonin (5HT) -2A | Frontal cortex | $^3$H-Ketanserin ($1.5 \times 10^{-9}$ M) | Cinanserin ($1 \times 10^{-5}$ M) |

Reaction mixture of total 250 μl was prepared in triplicate in 96 well plates as detail given in Table 8. The reaction mixture were mixed thoroughly and incubated for 15 min. at 37° C. After incubation of 15 min. the content of each reaction was filtered under vacuum manifold attached with liquid handling system. Washed twice with 250 μl cold tris-HCl buffer, dried over night, 60 μl scintillation fluid (Microscint 'O', Packard, USA) was added to each well followed by counting of radio activity in terms of count per minute (CPM) on plate counter (Top Count-NXT, Packard, USA). Percent inhibition of receptor binding was calculated in presence and absence of test sample.

$$\% \text{ Inhibition in binding} = \frac{\text{Binding in presence of test sample}}{\text{Total binding obtained in absence of test sample}} \times 100$$

TABLE 8

Details of buffer, competitors and *Rauwolfia tetraphylla* extracts/alkaloids added in the multiwell plates.

| Receptor Binding | Tris Buffer (40 mM) pH 7.4 | Radioligand | Membrane | Competitor | Samples | Total volume |
|---|---|---|---|---|---|---|
| Total Binding | 160 μl | 40 μl | 50 μl | — | — | 250 μl |
| Competitors | 140 μl | 40 μl | 50 μl | 20 μl | — | 250 μl |

TABLE 8-continued

Details of buffer, competitors and *Rauwolfia tetraphylla* extracts/alkaloids added in the multiwell plates.

| Receptor Binding | Tris Buffer (40 mM) pH 7.4 | Radioligand | Membrane | Competitor | Samples | Total volume |
|---|---|---|---|---|---|---|
| Binding with test sample | 140 µl | 40 µl | 50 µl | — | 20 µl (20 µg) | 250 µl |

Incubation was carried out in a final volume of 250 µl.

The inhibition potential of various *Rauwolfia tetraphylla* leaf extracts and fractions on the binding of 3H-Spiperone to corpus striatal and 3H-Ketanserin to frontocortical membranes were in-vitro screened and IC50 values were determined. The results are presented below in Table 9.

TABLE 9

Potential of extracts/fractions in inhibiting binding of 3H-Spiperone to corpus striatal and 3H-Ketanserin to frontocortical membranes following in vitro screening and IC50 values

| Extract/Fraction Code | Concentration (µg) | % Inhibition in binding 3H-Spiperone Dopamine | 3H-Ketanserin Serotonin |
|---|---|---|---|
| MeOH extract (1A)* | 50 µg | 69.24 | 78.25 |
|  | 25 µg | 61.64 | 63.21 |
|  | 12.5 µg | 48.77 | 60.31 |
|  | 6.25 µg | 38.99 | 54.30 |
|  | 3.12 µg | 28.82 | 31.47 |
|  | IC50 (µg) | 12.73 | 7.41 |
| Hexane fract. (1B)* | 50 µg | 83.14 | 91.92 |
|  | 25 µg | 83.26 | 86.55 |
|  | 12.5 µg | 70.78 | 74.54 |
|  | 6.25 µg | 61.38 | 67.14 |
|  | 3.12 µg | 47.49 | 60.96 |
|  | IC50 (µg) | 6.98 | ND |
| EtOAc fract. (1C)* | 50 µg | 71.04 | 65.46 |
|  | 25 µg | 67.43 | 65.89 |
|  | 12.5 µg | 64.22 | 60.22 |
|  | 6.25 µg | 56.24 | 50.97 |
|  | 3.12 µg | 46.71 | 52.75 |
|  | IC50 (µg) | 3.40 | 11.74 |
| BuOH fract. (1D)* | 50 µg | 70.39 | 65.02 |
|  | 25 µg | 59.58 | 64.72 |
|  | 12.5 µg | 58.04 | 60.14 |
|  | 6.25 µg | 52.25 | 56.07 |
|  | 3.12 µg | 49.80 | 44.79 |
|  | IC50 (µg) | 3.93 | 3.90 |
| Aqueous fract. (1E)* | 50 µg | 71.81 | 67.01 |
|  | 25 µg | 64.47 | 66.67 |
|  | 12.5 µg | 58.04 | 48.16 |
|  | 6.25 µg | 45.30 | 46.22 |
|  | 3.12 µg | 35.90 | 34.72 |
|  | IC50 (µg) | 8.35 | 10 |
| CHCl₃ fract. (2C)$ | 50 µg | 76.31 | 73.97 |
|  | 25 µg | 72.20 | 71.29 |
|  | 12.5 µg | 64.86 | 61.64 |
|  | 6.25 µg | 60.23 | 60.57 |
|  | 3.12 µg | 56.24 | 50.45 |
|  | IC50 (µg) | ND | 2.42 |

*Taken from Example 2.
$Taken from Example 4
IC50 values were calculated using different concentrations of extracts (3.12 to 50 µg) involving binding assays for 3H-spiperone to corpus striatal and 3H-ketanserin to frontocortical membranes.

From the Table 6, it is evident that $CHCl_3$ fraction at pH 9 (2C) was most active followed by EtOAc (1C), BuOH (1D), hexane (1B), aqueous (1E) fractions and methanol extract (1A) respectively. Similarly In-vitro screening of two commonly used antipsychotics, risperidone and olanzapine was carried out on DA-D2, 5-HT 2A and cholinergic receptors at various concentrations and the results are shown below in table-10:

TABLE 10

In Vitro effect of known Psychotics

| Binding/Drug | Concentration (ug) |  |  |  |  |  |
|---|---|---|---|---|---|---|
|  | 100 | 50 | 25 | 12.5 | 6.25 | 3.12 |
|  | % inhibition in binding |  |  |  |  |  |
| DA-D2 receptor |  |  |  |  |  |  |
| Risperidone | 75 | 70 | 67 | 61 | 55 | 52 |
| Olanzapine | 59 | 54 | 49 | 32 | 25 | 27 |
| 5-HT2A receptor |  |  |  |  |  |  |
| Risperidone | 70 | 70 | 67 | 59 | 59 | 58 |
| Olanzapine | 59 | 53 | 50 | 44 | 38 | 27 |
| Cholinergic receptor |  |  |  |  |  |  |
| Risperidone | 15 | 12 | 07 | 08 | 04 | 05 |
| Olanzapine | 87 | 83 | 75 | 65 | 50 | 37 |

Values are mean of three assays in each case.
Neurotransmitter receptor binding was carried out involving radioligand receptor assays.

Example-7

In Vivo Antipsychotic Screening

Figure 7:
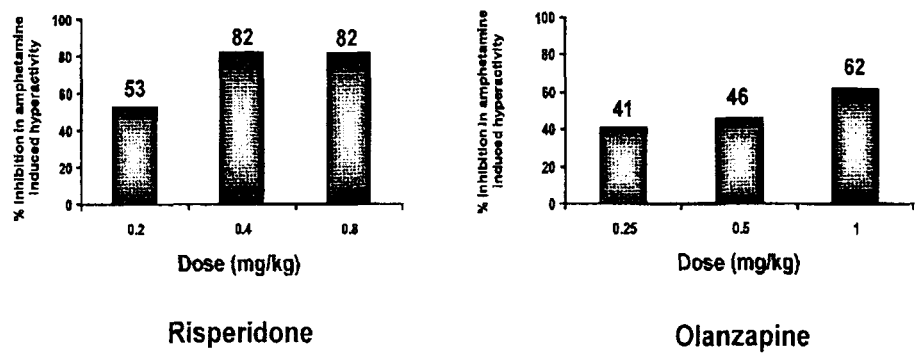
FIG. 7: Anti-psychotic activity evaluation of known drugs

A known drug of Risperidone can potentially cause tardive dyskinesia (TD), extrapyramidal symptoms (EPS) and neuroleptic malignant syndrome (NMS). Risperidone may also trigger diabetes and more serious conditions of glucose metabolism, including ketoacidosis and hyperosmolar coma. Another known drug olanzapine can cause tardive dyskinesia and rare, but life-threatening, neuroleptic malignant syndrome, Aggressiveness, akathisia inability to remain still, dry mouth, dizziness, irritability, sedation, insomnia, urinary retention, orthostatic hypotension, weight gain (90% of users experience weight gain, increased appetite, runny nose, low blood pressure, impaired judgment, thinking, and motor skills, impaired spatial orientation, impaired responses to senses, seizure, trouble swallowing, dental problems and discoloration of teeth, missed periods, problems with keeping body temperature regulated, apathy, lack of emotion, euphoria, Endocrine side effects have included hyperprolactinemia, hyperglycemia, diabetes mellitus, Hyperprolactinemia causing sexual dysfunction, menstrual irregularities, and osteoporosis. Anti-pshycotic activity of known drugs is shown in FIG. 7.

Although the doses of standard drugs are less in comparison to our antipsychotic standardized extracts and molecules but the standard drugs are having serious extrapyramidal symptoms (EPS) as side effects while our extracts and molecules are devoid of such side effects. This is the beauty and novelty of our extracts and molecules. In this way our extracts and molecules seems better than the standard drugs.

Animals:

In order to assess the antipsychotic potential of MeOH extract, its various fractions, alkaloids isolated and their derivatives from *Rauwolfia tetraphylla* leaf, amphetamine induced hyper activity mouse model was used following the method of Szewczak et al (1987). Adult Swiss mice of either sex (25±2 g body weight) obtained from the Indian Institute of Toxicology Research (IITR), Lucknow, India animal-breeding colony were used throughout the experiment. The animals were housed in plastic polypropylene cages under standard animal house conditions with a 12 hours light/dark cycle and temperature of 25±2° C. The animals had adlibitum access to drinking water and pellet diet (Hindustan Lever Laboratory Animal Feed, Kolkata, India). The Animal Care and Ethics Committee of IITR approved all experimental protocols applied to animals.

Antipsychotic Activity:

The mice randomly grouped in batches of seven animals per group. The basal motor activity (distance traveled) of each mouse was recorded individually using automated activity monitor (TSE, Germany). After basal activity recording, a group of seven animals were challenged with amphetamine [5.5 mg/kg, intra peritoneal (i.p) dissolved in normal saline]. After 30 min. amphetamine injection, motor activity was recorded for individual animal for 5 min. In order to assess the anti-psychotic activity of test samples of *R. tetraphylla*, already acclimatized animals were pre-treated with test sample (suspended in 2% gum *acacia* at a dose of 25, 12.5, 6.25 mg/kg given orally by gavage. One hour after sample treatment, each mouse were injected 5.5 mg/kg amphetamine i.p. 30 minutes after amphetamine treatment, motor activity was recorded of individual mouse for 5 min.

The difference in motor activity as indicated by distance traveled in animals with amphetamine alone treated and animals with samples plus amphetamine challenge was recorded as inhibition in hyperactivity caused by amphetamine and the data presented as percent inhibition in amphetamine induced hyperactivity.

Similarly In vivo screening of two commonly used antipsychotics, reseridone and olanzapine was carried out on amphetamine induced hyperactivity mice model and results are shown in FIG. 7

Human Dose

The minimum dose at which an antipsychotic molecule from *R. tetraphylla* showed >60% inhibition in amphetamine induced hyperactivity mice model was taken for human dose calculation.

The human dose of antipsychotic is 1/12 of the mice dose. Taking 60Kg as an average weight of a healthy human, human doses for antipsychotic natural agents from *R. tetraphylla* and their semi-synthetic derivatives were calculated as shown below.

$$\text{Human dose} = \frac{M^* \times 60^@}{12^\$} \text{ Or } M^* \times 5$$

Figure 5:
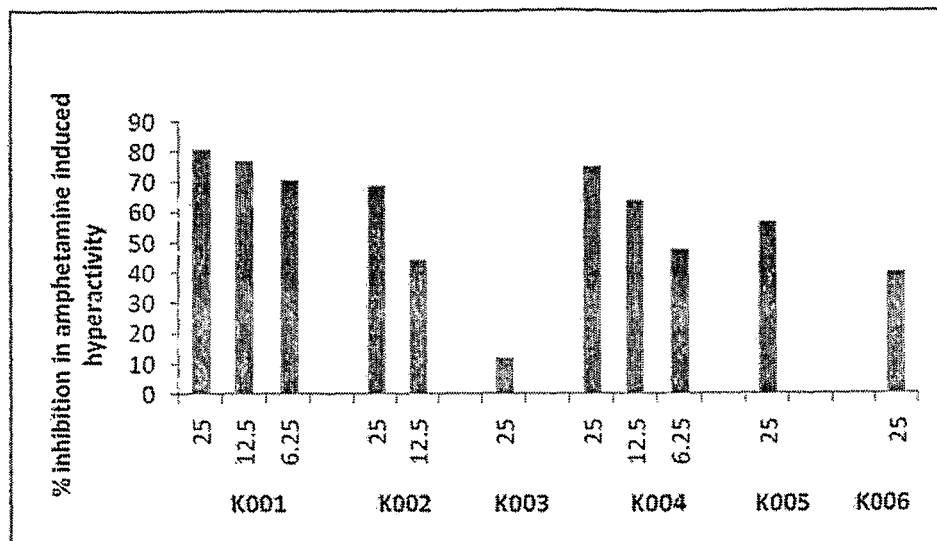
FIG. 5: Antipsychotic activity of purified alkaloids from the leaves of *Rauwolfia tetraphylla*

$M^*$ Dose in amphetamine induced hyperactivity mice model $^@$Average weight of a healthy human $^\$$Human dose is $\frac{1}{12}$ of the mice In FIG. 5, α-yohimbine at 6.25 mg/Kg showed >60% inhibition in amphetamine induced hyperactivity mice model. Hence the human dose of α-yohimbine will be $$\frac{6.25 \times 60}{12} = 31.25 \text{ mg}$$

The dosage of reserpiline for human is in the range of 125 mg to 140 mg. The dosage of 10-demethoxy reserpiline and 11-demethoxy reserpiline for human is in the range of 60 mg to 75 mg.

Example-8

Physiological and Biochemical Profile of Methanol Extract of *Rauwolfia tetraphylla* Leaves The effect of methanol extract of *Rauwolfia tetraphylla* leaves on the various physiological and biochemical parameters of Swiss albino mice was studied. The MeOH extract in 10, 100 & 300 mg/Kg body weight was administered through gastric intubation and the study was conducted for 28 days on animals of 7 animals per group. The results on various physiological and biochemical parameters are presented in Tables 11-15.

TABLE 11

Effect of MeOH extract on total RBC's count in Swiss albino mice.

| Treatment groups | RBCs(million/mm$^3$) |
|---|---|
| Vehicle control | 4.23 ± 0.17 |
| MeOH extract (1A) (10 mg) | 4.42 ± 0.95 |
| MeOH extract (1A) (100 mg) | 5.22 ± 0.58 |
| MeOH extract (1A) (300 mg) | 5.93 ± 0.41* |

TABLE 12

Effect of MeOH extract on total WBC's count in Swiss albino mice.

| Treatment groups | WBCs/mm$^3$ |
|---|---|
| Vehicle control | 14637.5 ± 2390.639 |
| MeOH extract (1A) (10 mg) | 9562.5 ± 1234.972 |
| MeOH extract (1A) (100 mg) | 12050 ± 2644.727 |
| MeOH extract (1A) (300 mg) | 12100 ± 2260.992 |

TABLE 13

Effect of MeOH extract on total Bilirubin levels in Swiss albino mice.

| Treatment groups | Total Bilirubin (mg/dl) |
|---|---|
| Vehicle control | 2.37 ± 0.22 |
| MeOH extract (1A) (10 mg) | 2.62 ± 0.26 |
| MeOH extract (1A) (10 mg) | 1.41 ± 0.22* |
| MeOH extract (1A) (10 mg) | 1.70 ± 0.19* |

TABLE 14

Effect of MeOH extract on Creatinine levels in Swiss albino mice.

| Treatment groups | Creatinine (mg/dl) |
|---|---|
| Vehicle control | 0.51 ± 0.07 |
| MeOH extract (1A) (10 mg) | 0.54 ± 0.03 |
| MeOH extract (1A) (100 mg) | 0.34 ± 0.05* |
| MeOH extract (1A) (300 mg) | 0.42 ± 0.03 |

TABLE 15

Effect of MeOH extract on Serum glutamic oxaloacetate transaminase (SGOT) levels in Swiss albino mice.

| Treatment groups | SGOT(U/l) |
|---|---|
| Vehicle control | 74.29 ± 10.73 |
| MeOH extract (1A) (10 mg) | 98.33 ± 10.16 |
| MeOH extract (1A) (100 mg) | 91.00 ± 4.57 |
| MeOH extract (1A) (300 mg) | 94.67 ± 13.80 |

From the Table 11-15, it is evident that MeOH extract (1A) of *Rauwolfia tetraphylla* leaves is non toxic and safely can be used in herbal formulation for human use.

Thus the herbal preparations of *Rauwolfia tetraphylla* leaves and the compounds isolated from its active fractions, exhibited significant antipsychotic activity on neurotransmitter receptor binding assay for dopaminergic-$D_2$ and Serotonergic ($5HT_{2A}$) receptors, involved in psychotic behavior. Further confirmation of antipsychotic activity in the above extracts and compounds was made on amphetamine induced mouse model in vivo. The present findings suggests that MeOH extract, ethylacetate and chloroform fractions of *R. tetraphylla* and the isolated compounds α-yohimbine, reserpiline and in a mixture 10-demethoxyreserpiline and 11-demethoxyreserpiline in 1:1.5 ratios can be used for treating psychotic conditions in human being without any extra pyramidal symptoms (EPS)

We claim:

1. A bioactive extract obtained from *Rauwolfia*, comprising:
   (a) from 13% to 22% by weight isoreserpiline,
   (b) from 15% to 43% by weight reserpiline,
   (c) from 1% to 15% by weight 11-demethoxy reserpiline and 10-demethoxy reserpiline,
   (d) from 3% to 22% by weight 10-methoxytetrahydroalstonine, and
   (e) from 10% to 39% by weight α-yohimbine.

2. The bioactive extract of claim 1, wherein said extract is an alcohol extract, and contains:
   (a) from 18% to 22% by weight isoreserpiline,
   (b) from 15% to 19% by weight reserpiline,
   (c) from 1% to 5% by weight 11-demethoxy reserpiline and 10-demethoxy reserpiline,
   (d) from 18% to 22% by weight 10-methoxytetrahydroalstonine, and
   (e) from 35% to 39% by weight α-yohimbine.

3. An ethyl acetate fraction of the extract of claim 1, comprising:
   (a) from 13% to 17% by weight isoreserpiline,
   (b) from 28% to 32% by weight reserpiline,
   (c) from 3% to 8% by weight 11-demethoxy reserpiline and 10-demethoxy reserpiline,
   (d) from 10% to 20% by weight 10-methoxytetrahydroalstonine, and
   (e) from 17% to 21% by weight α-yohimbine.

4. A chloroform fraction of the extract of claim 1, comprising:
   (a) from 14% to 18% by weight isoreserpiline,
   (b) from 39% to 43% by weight reserpiline,
   (c) from 9% to 14% by weight 11-demethoxy reserpiline and 10-demethoxy reserpiline,
   (d) from 7% to 12% by weight 10-methoxytetrahydroalstonine, and
   (e) from 10% to 15% by weight α-yohimbine.

5. The bioactive extract of claim 1, wherein said *Rauwolfia* is selected from the group consisting of *R. serpentine, R. carnesceus, R. vomitoria*, and *R. tetraphylla*.

6. A process for preparing the extract of claim 3, comprising:
   (a) powdering a sample of *Rauwolfia*,
   (b) extracting a powder produced in (a) in at least one of methanol or ethanol for from 16-20 hours,
   (c) filtering said extract,
   (d) evaporating the methanol or ethanol under reduced pressure to form an alcohol free extract,
   (e) testing bioactivity of said alcohol free extract to identify a non-toxic, antipsychotic *Rauwolfia* extract,
   (f) extracting any alcohol free extract determined to be non-toxic and antipsychotic with a 2%-5% acidic solution,
   (g) defatting the product of (f) with an organic solvent,
   (h) basifying the product of (g) at a temperature of from 3° C. to 8° C.,
   (i) extracting the product of (h) with a solvent selected from the group consisting of dichloromethane, chloroform, ethyl acetate, and diethyl ether, and
   (j) washing the product of (i) with water followed by drying over anhydrous sodium sulfate and removing any solvent under a vacuum, to obtain said fraction.

7. The method of claim 6, comprising extracting with chloroform in step (i).

8. The method of claim 6, further comprising subjecting the product of (j) to flash chromatography.

9. The method of claim 6, further comprising contacting the product of (j) with hexane and EtOAc at a 3:1 ratio to isolate tetrahydroalstonine, isoreserpiline, and an isomeric mixture of 10 and 11 demethoxy reserpiline, α-yohimbine, and reserpiline.

10. A process for preparing the bioactive fraction of claim 3, comprising:
    (a) powdering a sample of *Rauwolfia*,
    (b) extracting a powder produced in (a) in at least one of methanol or ethanol for from 16-20 hours,
    (c) filtering said extract,
    (d) evaporating the methanol or ethanol under reduced pressure to form an alcohol free extract,
    (e) dissolving said alcohol free extract in distilled water to form an aqueous solution,
    (f) filtering said aqueous solution,
    (g) subjecting said filtered, aqueous solution to successive extraction with hexane, ethyl acetate, and n-butanol, to obtain an organic fraction for each of hexane, ethyl acetate and n-butanol and an aqueous fraction,
    (h) combining said hexane and ethyl acetate fractions,
    (i) washing the combined fractions of (h),
    (j) drying the washed fraction of (i) over anhydrous sodium sulfate, to form an aqueous fraction,
    (k) distilling all solvents from all fractions to obtain a separate residue of each of said hexane, ethyl acetate, n-butanol, and aqueous fractions,
    (l) testing each separate residue for bioactivity, and
    (m) isolating α-yohimbine from said ethyl acetate fraction via chromatography.

11. The process of claim 10, wherein said chromatography comprises chromatography with hexane:EtOAc at a 1:1 ratio, hexane:EtOAc at a 65:35 residue, hexane:EtOAc at a 70:30 residue at t BuMe ether:ACN: water+0.8 mM TFA 4:1:5 ratio.

12. The process of claim 10, comprising extracting said powder for 3-5 hours using continuous, hot soxhlet extraction.

13. The process of claim 10, comprising extracting said powder via continuous hot soxhlet extraction for from 3-5 hours.

14. The process of claim 6, wherein said acidic solution is a solution of acetic acid, citric acid, tartaric acid, HCl, $H_2SO_4$, $H_3PO_4$ or $HNO_3$.

15. The process of claim 14, wherein said acidic solution is an HCl solution.

16. The process of claim 6, wherein said organic solvent is petroleum ether, hexane, dichloromethane, chloroform, ethyl acetate, or diethyl ether.

17. The process of claim 16, wherein said organic solvent is hexane.

18. The process of claim 6, comprising basifying the product of (g) with a solution of ammonia, sodium bicarbonate, sodium carbonate, sodium hydroxide, or potassium hydroxide.

19. The process of claim 18, comprising basifying with sodium carbonate.

20. The process of claim 6, comprising maintaining pH in step (h) at a pH from 8-12.

21. The process of claim 20, comprising maintaining the pH at 9.

* * * * *